United States Patent
Maruyama et al.

(10) Patent No.: US 6,462,081 B1
(45) Date of Patent: Oct. 8, 2002

(54) 5-THIA-ω-SUBSTITUTED PHENYL-PROSTAGLANDIN E DERIVATIVES, PROCESS FOR PRODUCING THE SAME AND DRUGS CONTAINING THE SAME AS THE ACTIVE INGREDIENT

(75) Inventors: Toru Maruyama, Ibaraki; Shuichi Ohuchida, Kyoto, both of (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/720,675
(22) PCT Filed: Jul. 14, 1999
(86) PCT No.: PCT/JP99/03798
§ 371 (c)(1), (2), (4) Date: Dec. 29, 2000
(87) PCT Pub. No.: WO00/03980
PCT Pub. Date: Jan. 27, 2000

(30) Foreign Application Priority Data

Jul. 15, 1998 (JP) .............................. 10-200752

(51) Int. Cl.⁷ ..................... C07C 405/00; A61K 31/557
(52) U.S. Cl. ...................... 514/530; 514/573; 560/15; 562/426
(58) Field of Search ................ 560/15; 562/426; 514/530, 573

(56) References Cited

U.S. PATENT DOCUMENTS 5,164,412 A    11/1992  Konishi et al.

FOREIGN PATENT DOCUMENTS

| EP | 0737676 | 10/1996 |
| JP | 58198466 | 11/1983 |
| JP | 6379870 | 4/1988 |

*Primary Examiner*—Robert Gerstl
(74) *Attorney, Agent, or Firm*—Stevens, Davis, Miller & Mosher, L.L.P.

(57) ABSTRACT

The present invention relates to 5-thia-ω-substituted phenylprostaglandin E derivatives of the formula (I)

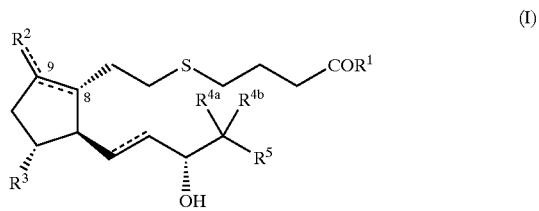

(wherein, all the symbols are as defined in the specification), process for producing them and pharmaceutical compositions comprising them as active ingredient.

The compounds of the formula (I) can bind to $PGE_2$ receptors (especially, subtype $EP_4$) strongly, so they are expected to be useful for prevention and/or treatment of immunological diseases (autoimmune diseases such as amyotrophic lateral sclerosis (ALS), multiple sclerosis, Sjoegren's syndrome, chronic rheumarthrosis and systemic lupus erythematosus etc., and rejection after organ transplantation etc.), asthma, abnormal bone formation, neuronal cell death, lung failure, liver damage, acute hepatitis, nephritis, renal insufficiency, hypertension, myocardial ischemia, systemic inflammatory response syndrome, ambustion pain, sepsis, hemophagous syndrome, macrophage activation syndrome, Still's disease, Kawasaki disease, burn, systemic granulomatosis, ulcerative colitis, Crohn's disease, hypercytokinemia at dialysis, multiple organ failure, and shock etc. Further, it is thought that $EP_4$ subtype receptor relates to sleeping disorder and blood platelet aggregation, so the compounds of the present invention are expected to be useful for the prevention and/or treatment of such diseases.

21 Claims, No Drawings

5-THIA-ω-SUBSTITUTED PHENYL-PROSTAGLANDIN E DERIVATIVES, PROCESS FOR PRODUCING THE SAME AND DRUGS CONTAINING THE SAME AS THE ACTIVE INGREDIENT

FIELD OF THE ART

The present invention relates to 5-thia-ω-substituted phenylprostaglandin E derivatives.

More particularly, it relates to 5-thia-ω-substituted phenylprostaglandin E derivatives of the formula (I)

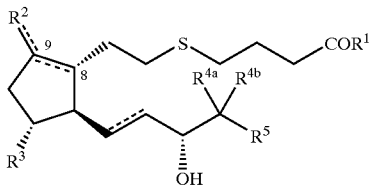

(wherein, all the symbols are as defined hereafter).

BACKGROUND OF THE ART

Prostaglandin $E_2$ (abbreviated as $PGE_2$) has been known as a metabolite in the arachidonate cascade. It has been known that $PGE_2$ possesses cyto-protective activity, uterine contractile activity, a pain-inducing effect, a promoting effect on digestive peristalsis, an awakening effect, a suppressive effect on gastric acid secretion, hypotensive activity and diuretic activity etc.

In the recent study, it was found that $PGE_2$ receptor was divided into some subtypes which possess different physical role from each other. At present, four receptor subtypes are known and they are called $EP_1$, $EP_2$, $EP_3$, $EP_4$ (Negishi M. et al, J. Lipid Mediators Cell Signaling, 12, 379–391 (1995)).

The present inventors have studied to find the compound which can bind to each receptor specifically, have found that the compound of the present invention can bind to $EP_4$ subtype receptor strongly, and then have achieved the present invention.

It is thought that $EP_4$ subtype receptor relates to inhibition of producing TNF-α and acceleration of producing IL-10. Therefore, the compounds of the present invention which can bind $EP_4$ subtype receptor strongly are expected to be useful for the prevention and/or treatment of immunological diseases (autoimmune diseases such as amyotrophic lateral sclerosis (ALS), multiple sclerosis, Sjoegren's syndrome, chronic rheumarthrosis and systemic lupus erythematosus etc., and rejection after organ transplantation etc.), asthma, abnormal bone formation, neuronal cell death, lung failure, liver damage, acute hepatitis, nephritis, renal insufficiency, hypertension, myocardiac ischemia, systemic inflammatory response syndrome, ambustion pain, sepsis, hemophagous syndrome, macrophage activation syndrome, Still's disease, Kawasaki disease, burn, systemic granulomatosis, ulcerative colitis, Crohn's disease, hypercytokinemia at dialysis, multiple organ failure, and shock etc.

Further, it is thought that $EP_4$ subtype receptor relates to sleeping disorder and blood platelet aggregation, so the compounds of the present invention are expected to be useful for the prevention and/or treatment of such diseases.

The compounds of the present invention of the formula (I) bind weakly to the other subtype receptors and do not express other effects, so such compounds are expected to be an agent having less side effect.

On the other hand, a lot of prostaglandins in which carbon atom at 5th position in PG skeleton was replaced with sulfur atom and which carbon atom(s) in ω-chain was modified have been known. But among such prostaglandins, there has been no publication which disclosed prostaglandins possessing unsubstituted or substituted phenyl in the ω-chain of PG skeleton concretely.

For example, in Japanese Patent Application Kokai Sho 58-198466, it is disclosed that the following 5-thia-prostaglandin derivatives possess an activity of inhibition of blood plate aggregation. That is to say, it is disclosed that 5-thia-prostaglandins of the formula (A)

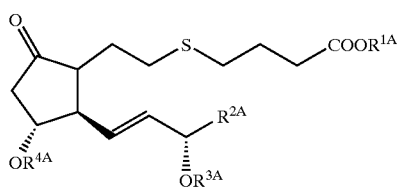

(wherein, $R^1$ is hydrogen or C1–10 alkyl,
$R^2$ is substituted or unsubstituted C1–10 alkyl or substituted or unsubstituted C5~6 cycloalkyl,
$R^3$ and $R^4$ are, same or differently, hydrogen or protecting group)
or non-toxic salts thereof when $R^1$ is hydrogen, possess an activity of inhibition of blood plate aggregation and a vasodilating activity, so they are useful as an agent for treatment or prevention of thrombosis and a hypertensive agent.

In this patent specification, the following ω-cyclopentyl-compound is shown in Example 3 as a concrete compound:

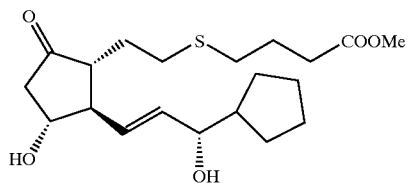

DISCLOSURE OF THE INVENTION

The present inventors have studied to find the stable compound which can bind to $EP_4$ receptor specifically and which can bind to neither the other EP subtype receptors nor the other prostanoid receptors.

From the results, they have found that 5-thiaprostaglandins modified by introducing substituted phenyl intoω-chain of the said prostaglandins meet these purposes, and then have achieved the present invention.

As mentioned later, they have found that the prostaglandin compounds in which 5th carbon atom of α-chain of PG skeleton is replaced with sulfur atom and in which phenyl substituted with a particular functional group is introduced into ω-chain of PG skeleton can bind to $EP_4$ strongly, bind to the other prostanoid receptors including the other subtype receptors weakly and are stable. And then, they have achieved the present invention.

The present invention relates to
(1) a 5-thia-ω-substituted phenyl-prostaglandin E derivative of the formula (I)

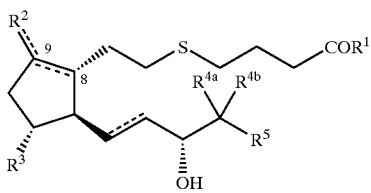

(I)

(wherein, $R^1$ is hydroxy, C1–6 alkyloxy or $NR^6R^7$ (in which $R^6$ and $R^7$ is, each independently, hydrogen or C1–4 alkyl),
$R^2$ is oxo, halogen or O—$COR^8$ (in which $R^8$ is C1–4 alkyl, phenyl or phenyl(C1–4 alkyl)),
$R^3$ is hydrogen or hydroxy,
$R^{4a}$ and $R^{4b}$ is, each independently, hydrogen or C1–4 alkyl,
$R^5$ is phenyl substituted with the following substituent(s):
 i) 1~3 of
  C1–4 alkyloxy-C1–4 alkyl,
  C2–4 alkenyloxy-C1–4 alkyl,
  C2–4 alkynyloxy-C1–4 alkyl,
  C3–7 cycloalkyloxy-C1–4 alkyl,
  C3–7 cycloalkyl(C1–4 alkyloxy)-C1–4 alkyl,
  phenyloxy-C1–4 alkyl,
  phenyl-C1–4 alkyloxy-C1–4 alkyl,
  C1–4 alkylthio-C1–4 alkyl,
  C2–4 alkenylthio-C1–4 alkyl,
  C2–4 alkynylthio-C1–4 alkyl,
  C3–7 cycloalkylthio-C1–4 alkyl,
  C3–7 cycloalkyl (C1–4 alkylthio)-C1–4 alkyl,
  phenylthio-C1–4 alkyl or
  phenyl-C1–4 alkylthio-C1–4 alkyl,
 ii) C1–4 alkyloxy-C1–4 alkyl and C1–4 alkyl,
  C1–4 alkyloxy-C1–4 alkyl and C1–4 alkyloxy,
  C1–4 alkyloxy-C1–4 alkyl and hydroxy,
  C1–4 alkyloxy-C1–4 alkyl and halogen,
  C1–4 alkylthio-C1–4 alkyl and C1–4 alkyl,
  C1–4 alkylthio-C1–4 alkyl and C1–4 alkyloxy,
  C1–4 alkylthio-C1–4 alkyl and hydroxy or
  C1–4 alkylthio-C1–4 alkyl and halogen,
 iii) haloalkyl or hydroxy-C1–4 alkyl, or
 iv) C1–4 alkyl and hydroxy;
----- is single bond or double bond,
with the proviso that when $R^2$ is O—$COR^8$, C8-C9 represents double bond) or a non-toxic salt thereof, or a cyclodextrin clathrate thereof,
(2) process for producing it, and
(3) a pharmaceutical composition comprising it as an active ingredient.

DETAILED EXPLANATION OF THE INVENTION

In the formula (I), C1–4 alkyl represented by $R^{4a}$, $R^{4b}$, $R^6$, $R^7$ and $R^8$ and C1–4 alkyl in $R^5$ and $R^8$ means methyl, ethyl, propyl, butyl and isomers thereof.

In the formula (I), C1–6 alkyl represented by $R^1$ means methyl, ethyl, propyl, butyl, pentyl, hexyl and isomers thereof.

In the formula (I), C2–4 alkenyl in $R^5$ means vinyl, propenyl, butenyl and isomers thereof.

In the formula (I), C2–4 alkynyl in $R^5$ means ethynyl, propynyl, butynyl and isomers thereof.

In the formula (I), C3–7 cycloalkyl in $R^5$ means cyclopropyl, cyclobutyl, cyclopentyl, cyclohexyl and cycloheptyl.

In the formula (I), halogen in $R^2$ and $R^5$ means fluoride, chloride, bromide and iodide.

In the present invention, the symbol ⫽ means single bond or double bond. Further, unless otherwise specified, in the present invention, the symbol ⫽ means that the substituent attached thereto is in front of the sheet, the symbol "⫽" means that the substituent attached thereto is behind the sheet and the symbol ⫽ or ⫽ means that there is a mixture of substituents in front of and behind the sheet or that the substituent attached thereto may be in front of or behind the sheet as would be clear to the person skilled in the art.

Unless otherwise specified, all isomers are included in the present invention. For example, alkyl, alkenyl, alkynyl, alkylene group means straight-chain or branched-chain ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomers (D-, L-, d-, l-isomer), polar compounds generated by chromatographic separation (more polar compound, less polar compound), equilibrium compounds, mixtures thereof at voluntary ratios and racemic mixtures are also included in the present invention.

In the formula (I), the substituent(s) of phenyl in $R^5$ is/are preferably attached at 3-position, 3-position and 4-position, or 3-position and 5-position.

In the formula (I), each group (i) to (iv) as the substituent (s) of phenyl in $R^5$ means as follows:

group i) means 1, 2 or 3 of alkyloxyalkyl etc.,
group ii) means at least one alkyloxyalkyl etc. and at least one alkyl, alkyloxy, hydroxy or halogen,
group iii) means alkyl substituted with 1 or 2 of halogen or hydroxy and
group iv) means at least one alkyl and at least one hydroxy.

Among the compounds of the present invention of the formula (I), the compounds described in the Examples, the compounds shown in the following Tables and the corresponding esters and amides are preferable.

TABLE 1

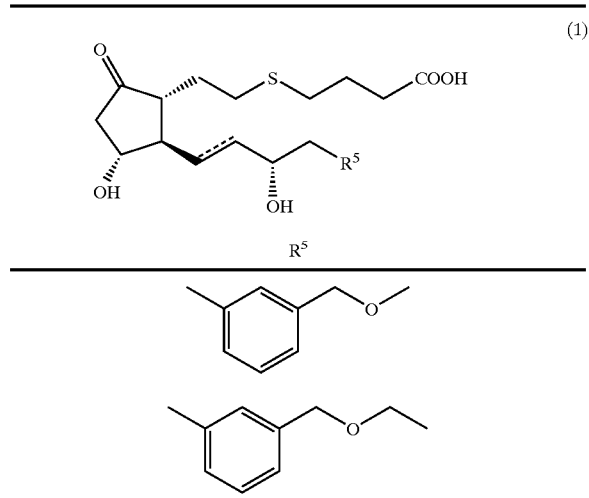

TABLE 1-continued
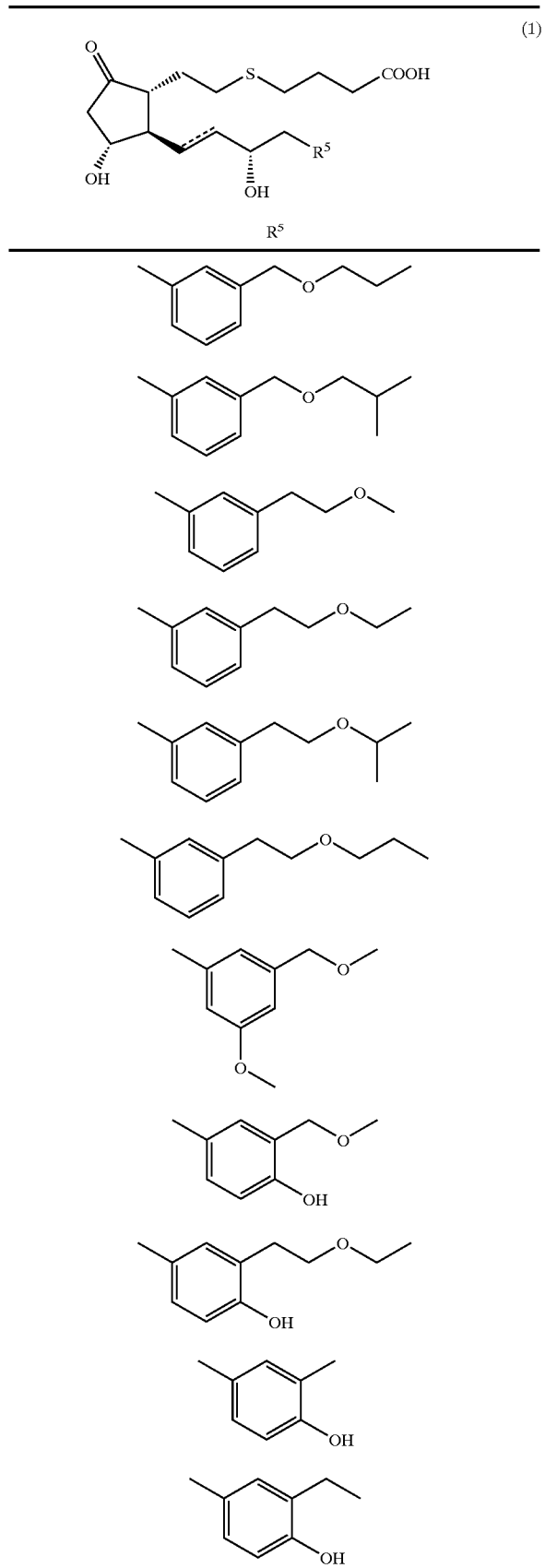
TABLE 1-continued
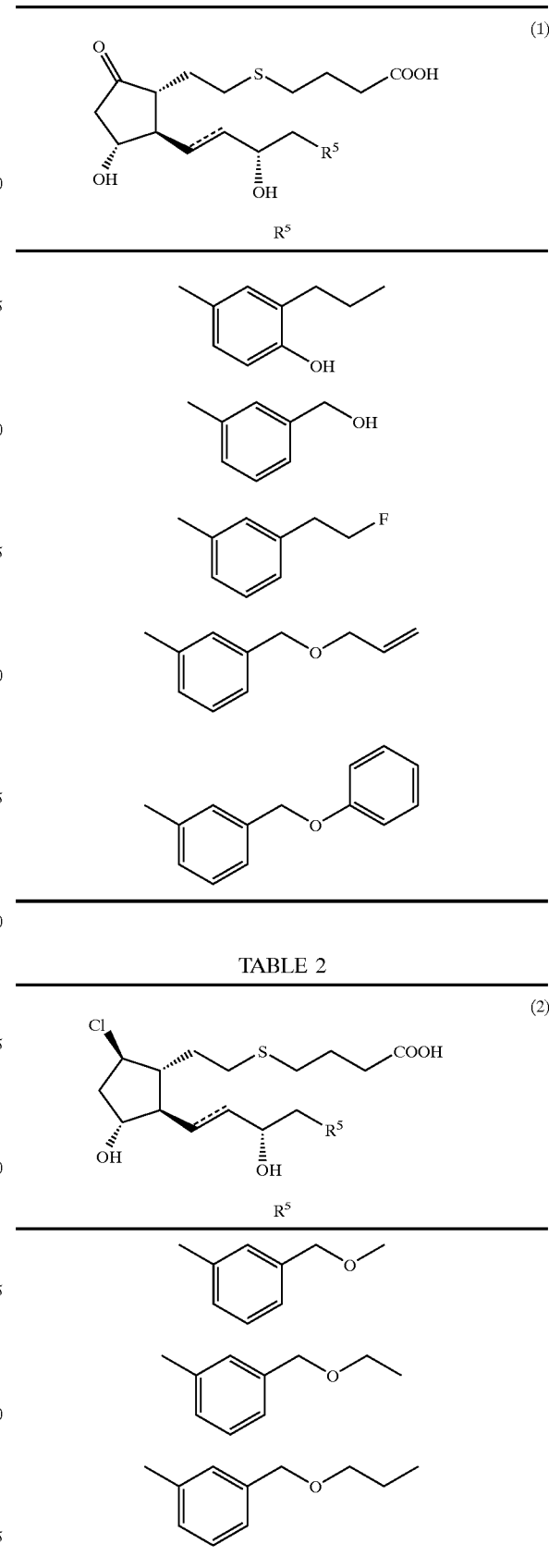
TABLE 2

TABLE 2-continued (2)

[Structure: Cyclopentane with Cl, OH substituents, vinyl-CH(OH)-CH2-R5 chain, and CH2CH2-S-CH2CH2CH2-COOH chain]

| R⁵ |
|---|
| 3-methylbenzyl isobutyl ether |
| 3-methylphenethyl methyl ether |
| 3-methylphenethyl ethyl ether |
| 3-methylphenethyl isopropyl ether |
| 3-methylphenethyl propyl ether |
| 3,5-dimethoxymethyl-methylbenzene derivative |
| 2-(methoxymethyl)-4-methylphenol |
| 2-(2-ethoxyethyl)-4-methylphenol |
| 2,4-dimethylphenol |
| 2-ethyl-4-methylphenol |
| 2-propyl-4-methylphenol |

TABLE 2-continued (2)

[Structure: Cyclopentane with Cl, OH substituents, vinyl-CH(OH)-CH2-R5 chain, and CH2CH2-S-CH2CH2CH2-COOH chain]

| R⁵ |
|---|
| 3-methylbenzyl alcohol |
| 1-(2-fluoroethyl)-3-methylbenzene |
| 3-methylbenzyl allyl ether |
| 3-methylbenzyl phenyl ether |

TABLE 3

(3)

[Structure: Cyclopentane with F, OH substituents, vinyl-CH(OH)-CH2-R5 chain, and CH2CH2-S-CH2CH2CH2-COOH chain]

| R⁵ |
|---|
| 3-methylbenzyl methyl ether |
| 3-methylbenzyl ethyl ether |
| 3-methylbenzyl propyl ether |
| 3-methylbenzyl isobutyl ether |

TABLE 3-continued (3)

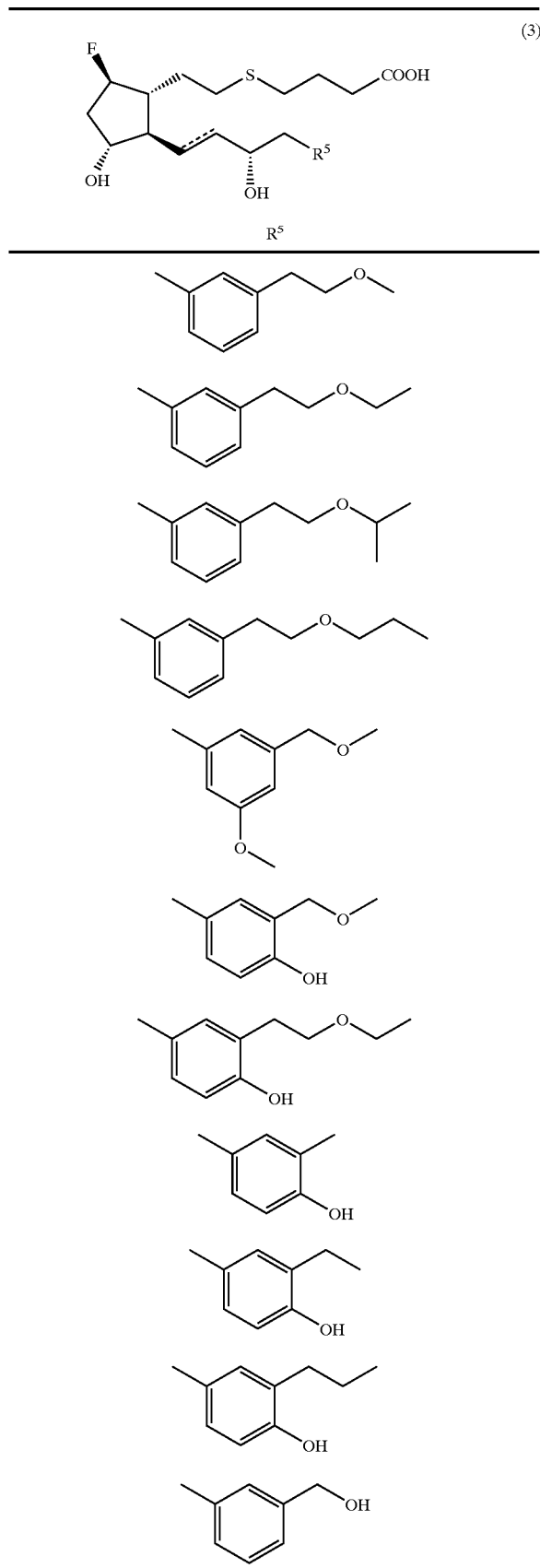

TABLE 3-continued (3)

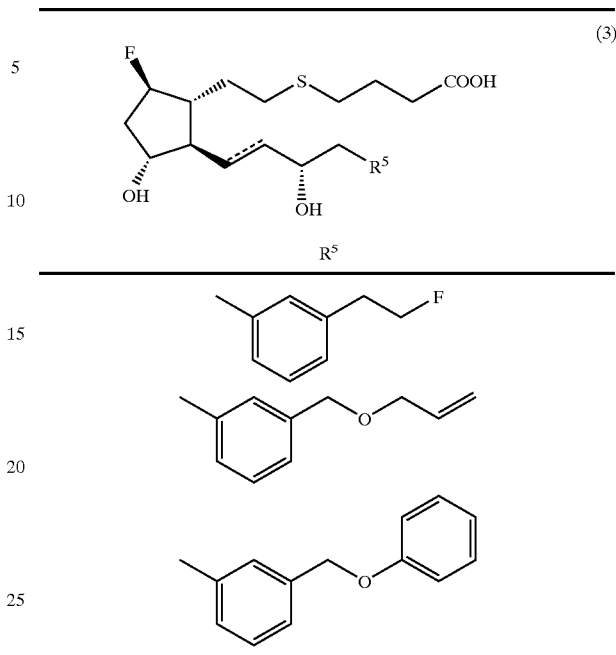

[Salts]

The compounds of the present invention of the formula (I) may be converted into the corresponding salts by known methods. Non-toxic and water-soluble salts are preferable. Suitable salts, for example, are as follows: salts of alkali metals (potassium, sodium etc.), salts of alkaline earth metals (calcium, magnesium etc.), ammonium salts, salts of pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.).

[Cyclodextrin Clathrate]

The compounds of the present invention of the formula (I) may be converted into the corresponding cyclodextrin clathrates by the method described in the specification of Japanese Patent Application Kokoku Sho 50-3362, 52-31404 or 61-52146 using α-, β- or γ-cyclodextrin or a mixture thereof. Converting into the corresponding cyclodextrin clathrates serves to increase the stability and solubility in water of the compounds, and therefore it is useful in the use for pharmaceuticals.

[Process for Producing the Compounds of the Present Invention]

(a) Compounds of the formula (I), wherein $R^1$ is C1–6 alkyloxy i.e., the compounds of the formula (Ia)

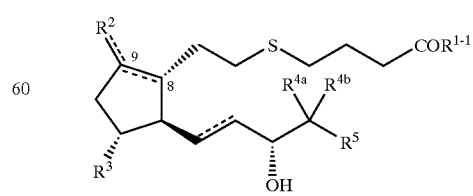

(Ia)

(wherein, $R^{1-1}$ is C1–6 alkyloxy and the other symbols are as defined hereinbefore)

may be prepared from the compounds of the formula (II)

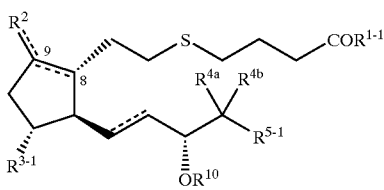
(II)

(wherein, $R^{3-1}$ is hydrogen or hydroxy protected by a protecting group which is removed under acidic conditions, $R^{10}$ is a protecting group of hydroxy which is removed under acidic conditions, $R^{5-1}$ is as defined for $R^5$, provided that hydroxy group in $R^{5-1}$ is protected by a protecting group which is removed under acidic conditions, and the other symbols are as defined hereinbefore) by the reaction for removal of a protecting group under acidic conditions.

The protecting group of hydroxy which is removed under acidic conditions includes, for example, t-butyldimethylsilyl, triphenylmethyl, tetrahydropyran-2-yl etc.

The hydrolysis under acidic conditions may be carried out by known methods. It may be carried out, for example, in an organic solvent miscible with water (e.g., tetrahydrofuran, methanol, ethanol, dimethoxyethane, acetonitrile or mixture thereof etc.) using an inorganic acid (e.g., hydrochloric acid, phospate, hydrofluoric acid, hydrogen fluoride-pyridine etc.), or an organic acid (e.g., acetic acid, tosylic acid, trichloroacetic acid etc.) at 0~50° C.

(b) Compounds of the formula (I), wherein $R^1$ is hydroxy i.e., the compounds of the formula (Ib)

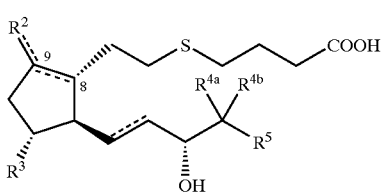
(Ib)

(wherein, all the symbols are as defined hereinbefore) may be prepared from the compounds of the formula (Ia)

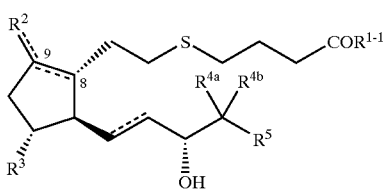
(Ia)

(wherein, all the symbols are as defined hereinbefore) by hydrogenolysis using an enzyme or by hydrogenolysis under alkaline conditions.

The hydrogenolysis using an enzyme may be carried out by known methods. It may be carried out, for example, in a mixed solvent of organic solvent miscible with water (e.g., ethanol, dimethylsulfoxide etc.) and water, in the presence or absence of buffer solution, using an enzyme for hydrogenolysis (esterase, lipase etc.) at 0~50° C.

The hydrogenolysis under alkaline conditions may be carried out by known methods. It may be carried out, for example, in an organic solvent miscible with water (e.g., ethanol, tetrahydrofuran (THF), dioxane etc.) using an aqueous solution of alkali (sodium hydroxide, potassium hydroxide, potassium carbonate etc.) at -10~90° C.

(c) Compounds of the formula (I), wherein $R^1$ is $NR^6R^7$ i.e., the compounds of the formula (Ic)

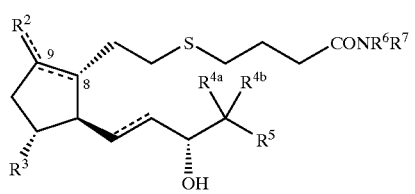
(Ic)

(wherein, all the symbols are as defined hereinbefore)

may be prepared by amidation of the compounds of the formula (Ib)

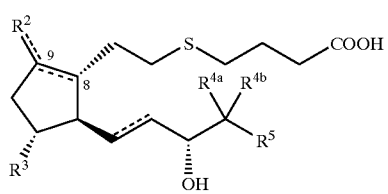
(Ib)

(wherein, all the symbols are as defined hereinbefore) with the compounds of the formula (III)

$HNR^6R^7$  (III)

(wherein, all the symbols are as defined hereinbefore).

Amidation may be carried out by known methods. For example, it may be carried out in an inert organic solvent (THF, methylene chloride, benzene, acetone, acetonitrile or mixture thereof etc.), in the presence or absence of a tertiary amine (dimethylaminopyridine, pyridine, triethylamine etc.), using a condensing agent (1,3-dicyclohexylcarbodiimide (DCC), 1-ethyl-3-[3-(dimethylamino)propyl] carbodiimide (EDC) etc.) at 0~50° C.

The compounds of the formula (III) have been known or may be prepared by known methods easily.

The compounds of the formula (II) may be prepared by the following Reaction Schemes 1–5.

In each Reaction Scheme, the symbols are as defined hereinbefore or are as follows:

t-Bu: t-butyl,

Et: ethyl,

Ms: methanesulfonyl,

DMAP: dimethylaminopyridine, n-Bu: normal butyl,

AIBN: 2,2'-azobisisobutyronitrile,

Ts: p-toluenesulfonyl, $R^{2-1}$: halogen,

Ac: acetyl,

TMS: trimethylsilyl.

Reaction Scheme 1
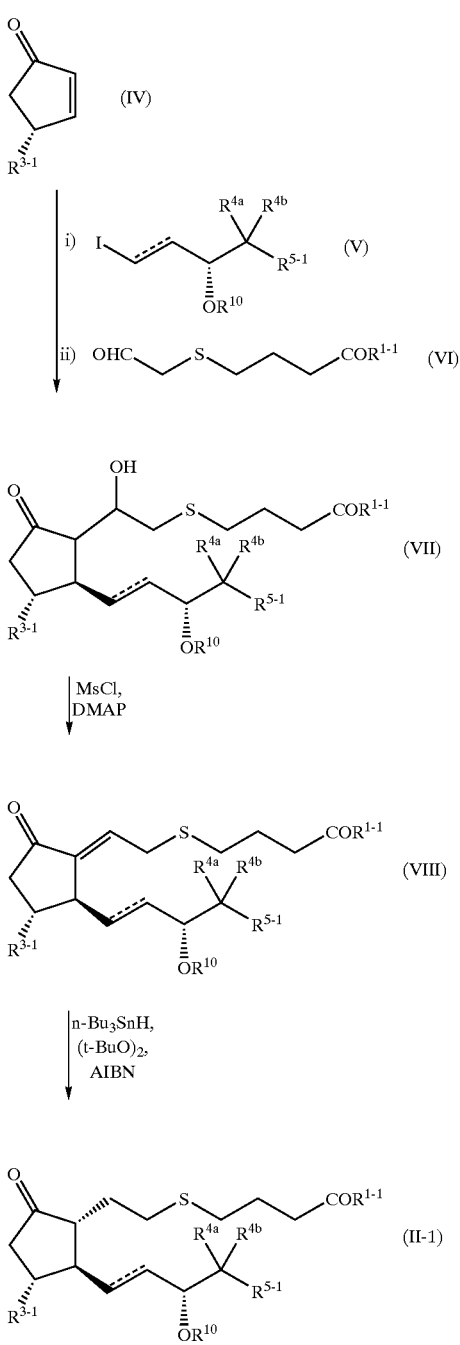
Reaction Scheme 2
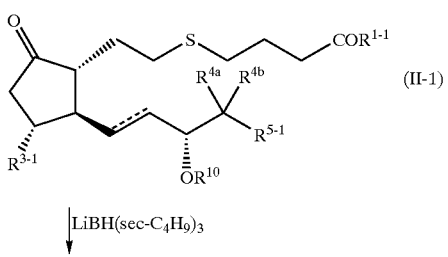
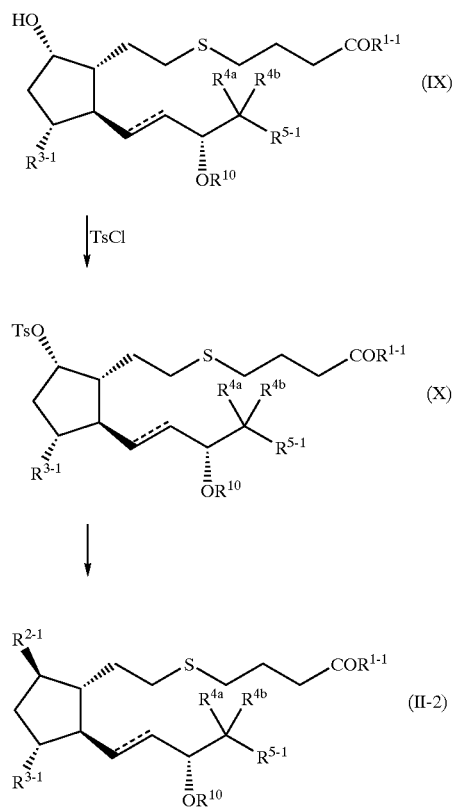
Reaction Scheme 3
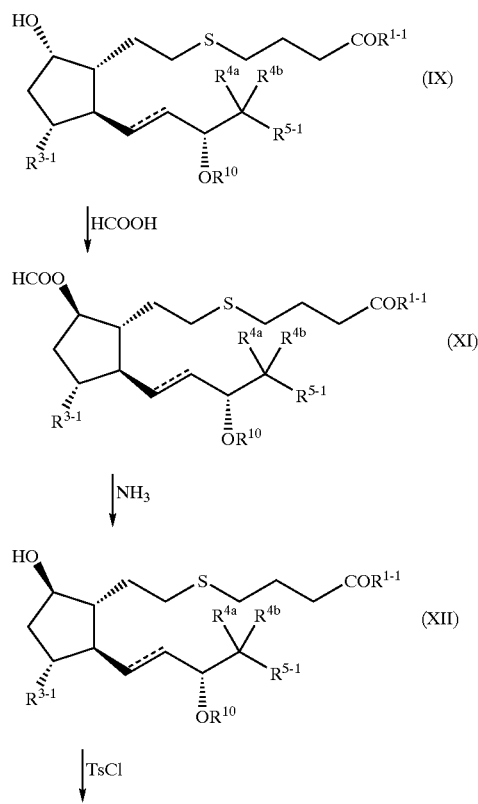

-continued
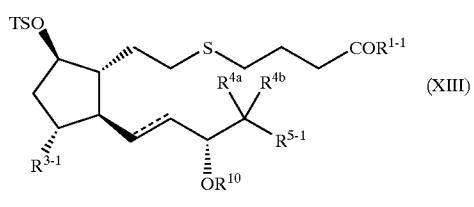
(XIII)
↓ halogenation
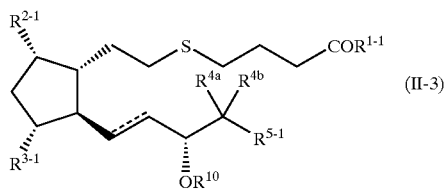
(II-3)
Reaction Scheme 4
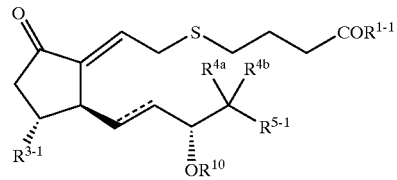
(VIII)
↓ 1) trialkyl hydride silane
2) $(R^8CO)_2O$ (XVI)
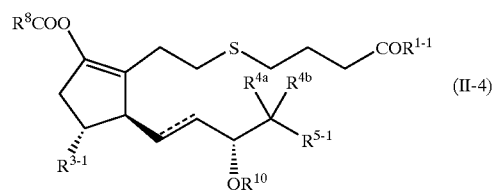
(II-4)
Reaction Scheme 5
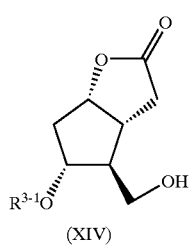 →Oxidation→ 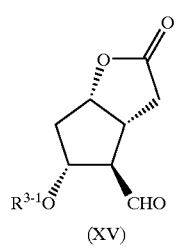 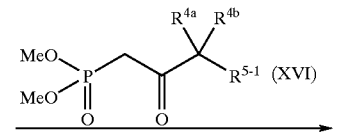 →
(XIV)  (XV)
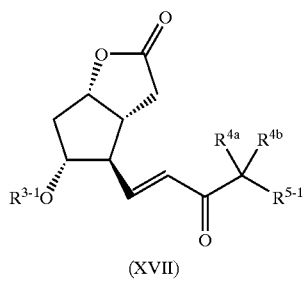 →Reduction→ 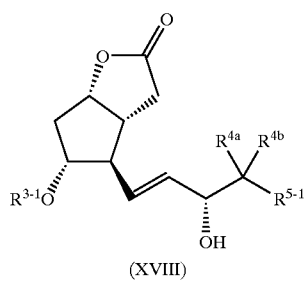 →Protection→
(XVII)  (XVIII)
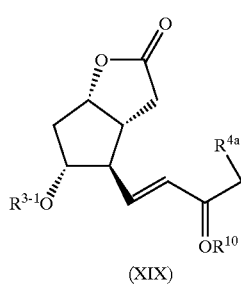 →Reduction→ ( 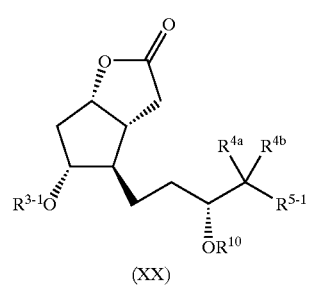 ) →Cleavage of ring→
(XIX)  (XX)

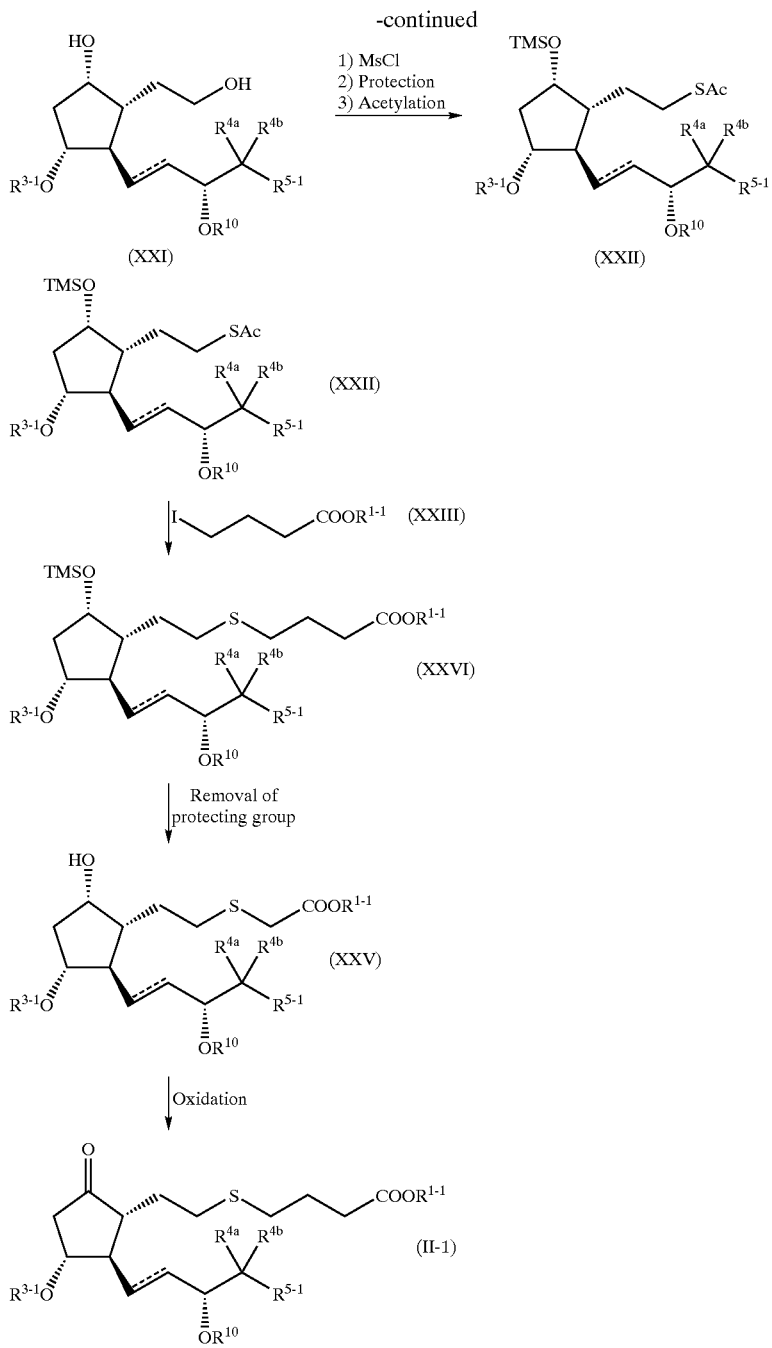

[Starting Materials and Reagents]

Each Reaction in the said Reaction Schemes may be carried out by known methods. In the said Reaction Schemes, the compounds of the formulae (IV), (V), (XVI), (XIV), (VI) and (XXIII) as starting materials have been known or may be prepared easily by known methods.

For example, the compounds of the formula (XIV) wherein $R^{3-1}$ is THP have been described in J. Am. Chem. Soc., 98, 1490 (1971).

The other starting materials and reagents in the present invention are known per se or may be prepared by known methods.

In each reaction in the present specification, reaction products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

[Pharmacological Activities]

The compounds of the present invention of the formula (I) can bind strongly and show an activity on the $EP_4$ subtype receptor which is one of the $PGE_2$ receptors.

For example, in a standard laboratory test, such effects of the compound of the present invention were confirmed by binding assay using cell expressing the prostanoid receptor subtypes. (i) Binding assay using cell expressing the prostanoid receptor subtypes The preparation of membrane fraction was carried out according to the method of Sugimoto et al (J. Biol. Chem., 267, 6463–6466 (1992)), using CHO cell expressing prostanoid receptor subtype (mouse $EP_1$, $EP_2$, $EP_3$, and $EP_4$, and human IP).

The reaction solution (200 μl) containing membrane fraction (0.5 mg/ml), [$^3$H]-$PGE_2$ was incubated for 1 hour at room temperature. The reaction was terminated by addition of 3 ml of ice-cold buffer. The mixture was rapidly filtered under reduced pressure through a glass filter (GF/B). The radioactivity associated with the filter was measured by liquid scintillation counter.

Kd and Bmax values were determined from Scatchard plots [Ann. N.Y. Acad. Sci., 51, 660 (1949)]. Non-specific binding was calculated as the amount bound in the presence of an excess (2.5 μM) of unlabeled $PGE_2$. In the experiment for competition of specific [$^3$H]-$PGE_2$ binding by the compounds of the present invention, [$^3$H]-$PGE_2$ was added at a concentration of 2.5 nM and the compound of the present invention was added at various concentrations. The following buffer was used in all reactions. Buffer: 10 mM potassium phosphate (pH6.0), 1 mM EDTA, 10 mM $MgCl_2$, 0.1 M NaCl The dissociation constant Ki (μM) of each compound was calculated by the following equation.

$$Ki=IC_{50}/(1+([C]/Kd))$$

The results are shown in Table 4.

TABLE 4

| Example Nos. | $EP_4$ Ki (μM) | $EP_1$ Ki (μM) | $EP_3\alpha$ Ki (μM) |
|---|---|---|---|
| 3 | 0.0038 | >10 | 0.84 |
| 3 (1) | 0.0024 | >10 | 2.9 |
| 3 (2) | 0.0079 | >10 | >10 |
| 3 (3) | 0.018 | >10 | 1.5 |
| 3 (4) | 0.01 | >10 | 0.5 |
| 3 (5) | 0.015 | >10 | 0.57 |
| 6 | 0.0062 | >10 | 0.46 |

As shown in the above results, the compounds of the present invention can bind to receptor for subtype $EP_4$ strongly and do not bind to other receptors for $PGE_2$.

[Toxicity]

The toxicity of the compounds of the formula (I) of the present invention is very low and therefore, it is confirmed that these compounds are safe for use as medicine. For example, the maximum tolerance dose of the compound of Example 1 by i.v. route in rat was 30 mg/kg body weight or more.

Industrial Application

The compounds of the present invention of the formula (I) can bind and show the activity on the $PGE_2$ receptor. Particularly, they bind $EP_4$ subtype receptor strongly, so they are useful for the prevention and/or treatment of immunological diseases (autoimmune diseases such as amyotrophic lateral sclerosis (ALS), multiple sclerosis, Sjoegren's syndrome, chronic rheumarthrosis and systemic lupus erythematosus etc., and rejection after organ transplantation etc.), asthma, abnormal bone formation, neuronal cell death, lung failure, liver damage, acute hepatitis, nephritis, renal insufficiency, hypertension, myocardiac ischemia, systemic inflammatory response syndrome, ambustion pain, sepsis, hemophagous syndrome, macrophage activation syndrome, Still's disease, Kawasaki disease, burn, systemic granulomatosis, ulcerative colitis, Crohn's disease, hypercytokinemia at dialysis, multiple organ failure, and shock etc. Further, it is thought that $EP_4$ subtype receptor relates to sleeping disorder and blood platelet aggregation, so the compounds of the present invention are expected to be useful for the prevention and/or treatment of such diseases.

The compounds of the present invention of the formula (I) bind weakly to the other subtype receptors and do not express other effects, therefore such compounds are expected to be an agent having less side effect.

For the purpose above described, the compounds of the formula (I) of the present invention, non-toxic salts thereof, or cyclodextrin clathrates thereof may be normally administered systemically or locally, usually by oral or parenteral administration (administration into joint or subcutaneous administration etc. is included).

The doses to be administered are determined depending upon age, body weight, symptom, the desired therapeutic effect, the route of administration, and the duration of the treatment etc. In the human adult, the doses per person per dose are generally between 1 μg and 100 mg, by oral administration, up to several times per day, and between 0.1 μg and 10 mg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

The compounds of the present invention may be administered as solid compositions, liquid compositions or other compositions for oral administration, or as injections, liniments or suppositories etc. for parenteral administration.

Solid compositions for oral administration include compressed tablets, pills, capsules, dispersible powders, and granules.

Capsules contain hard capsules and soft capsules.

In such compositions, one or more of the active compound(s) is or are, admixed with at least one inert diluent such as lactose, mannitol, mannit, glucose, hydroxypropyl cellulose, microcrystalline cellulose, starch, polyvinylpyrrolidone, magnesium metasilicate aluminate.

The compositions may also comprise, as is normal practice, additional substances other than inert diluents: e.g. lubricating agents such as magnesium stearate, disintegrating agents such as cellulose calcium glycolate, and agents to assist dissolution such as glutamic acid, asparaginic acid. The tablets or pills may, if desired, be coated with film of gastric or enteric material such as sugar, gelatin, hydroxypropyl cellulose or hydroxypropyl cellulose phthalate etc., or be coated with two or more films. And further, coating may include containment within capsules of absorbable materials such as gelatin.

Liquid compositions for oral administration include pharmaceutically-acceptable emulsions, solutions, syrups and elixirs etc. In such liquid compositions, one or more of the active compound(s) is or are comprised in inert diluent (s) commonly used in the art (for example, purified water, ethanol etc.). Besides inert diluents, such compositions may also comprise adjuvants such as wetting agents, suspending agents, sweetening agents, flavouring agents, perfuming agents and preserving agents.

Other compositions for oral administration include spray compositions which may be prepared by known methods and which comprise one or more of the active compound(s). Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. Nos. 2,868,691 or 3,095,355 may be used.

Injections for parenteral administration include ste rile aqueous or non-aqueous solutions, suspensions and emulsions. Aqueous solutions or suspensions include distilled water for injection and physiological salt solution. Non-aqueous solutions or suspensions include propylene glycol, polyethylene glycol, plant oil such as olive oil, alcohol such as ethanol, POLYSORBATE80 (registered trade mark) etc.

Such compositions may comprise additional diluents: e.g. preserving agents, wetting agents, emulsifying agents, dispersing agents, stabilizing agent, assisting agents such as agents to assist dissolution (for example, glutamic acid, asparaginic acid). They may be sterilized for example, by filtration through a bacteria-retaining filter, by incorporation of sterilizing agents in the compositions or by irradiation. They may also be manufactured in the form of sterile solid compositions which can be dissolved in sterile water or some other sterile diluent for injection immediately before use.

Other compositions for parenteral administration include liquids for external use, and endermic liniments, ointments, suppositories and pessaries which comprise one or more of the active compound(s) and may be prepared by known methods.

BEST MODE TO CARRY OUT THE INVENTION

The following Reference Examples and Examples are intended to illustrate, but not limit, the present invention.

The solvents in parentheses in chromatographic separations and TLC show the developing or eluting solvents and the ratios of the solvents used are by volume.

The solvents in parentheses in NMR show ones used for measurement.

REFERENCE EXAMPLE 1

1-Bromo-3-Methoxymethylbenzene

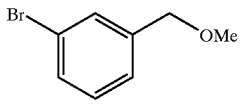

To a solution of 3-bromobenzyl bromide (15.0 g, 60 mmol) in methanol-dimethoxyethane (DME) (30 ml+10 ml), sodium methylate (4.9 g, 90 mmol) was added under cooling with ice. The mixture was stirred for 1 hour at room temperature. The reaction mixture was poured into water and extracted with ether. The organic layer was washed by an aqueous saturated solution of sodium chloride and dried over magnesium sulfate. The solvent was distilled off to obtain the title compound ( 12.1 g) having the following physical data.

TLC: Rf 0.74 (ethyl acetate:hexane=1:4); NMR (CDCl$_3$): δ 7.50 (s, 1H), 7.42 (dt, J=8, 2 Hz, 1H), 7.3–7.2 (m, 2H), 4.43 (s, 2H), 3.40 (s, 3H).

REFERENCE EXAMPLE 2

(2S)-3-(3-Methoxymethylphenyl)-1-triphenylmethoxypropan-2-ol

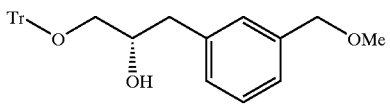

Magnesium (1.41 g, 58 mmol) was heated to dry under vacuum condition. Thereto, anhydrous tetrahydrofuran (THF) (30 ml) and dibromo ethane (a few drops) were added. A solution of a compound prepared in Reference Example 1 (9.65 g, 48 mmol) in anhydrous THF (30 ml) was added dropwise for 45 minutes. Thus obtained solution was added to a suspension of cuprous iodide (0.76 g, 4 mmol) in anhydrous THF (30 ml) under cooling with ice. The mixture was stirred for 30 minutes. Thereto, a solution of S-(–)-glycidyl triytyl ether (12.7 g, 40 mmol) in anhydrous THF (30 ml) was added. After stirring the mixture for 1 hour, the reaction mixture was poured into an aqueous saturated solution of ammonium chloride. The mixture was extracted with ethyl acetate. The organic layer was washed by an aqueous saturated solution of sodium chloride and dried over magnesium sulfate. The solvent was distilled off to obtain the title compound ( 19.5 g) having the following physical data.

TLC: Rf 0.29 (ethyl acetate:hexane=1:4); NMR (CDCl$_3$): δ (7.5–7.1 (m, 19H), 4.40 (s, 2H), 4.1–3.9 (m, 1H), 3.37 (s, 3H), 3.3–3.1 (m, 2H), 2.9–2.7 (m, 2H), 2.23 (br, 1H).

REFERENCE EXAMPLE 3

(2S)-3-(3-Methoxymethylphenyl)propan-1,2-diol

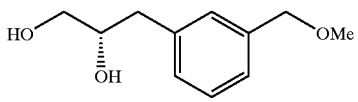

To a solution of a compound prepared in Reference Example 2 (19.5 g) in THF (10 ml), acetic acid (80 ml) and water (10 ml) were added. The mixture was heated for 6 hours at 60° C. and then cooled to room temperature by addition of water (40 ml). The precipitate was filtered. The filtrate was concentrated. The precipitate was filtered again. The oil compound which was obtained by concentration of the filtrate was distilled with toluene to remove the solvent and to obtain the title compound (8.9 g) having the following physical data.

TLC: Rf 0.64 (ethyl acetate:hexane=2:1).

REFERENCE EXAMPLE 4

(2S)-3-(3-Methoxymethylphenyl)-1-acetyloxypropan-2-ol

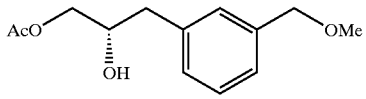

A solution of a compound prepared in Reference Example 3 (8.9 g) and 2,4,6-collidine (10.6 ml, 80 mmol) in methylene chloride (120 ml) was cooled to −70° C. Thereto, acetyl chloride (4.0 ml, 56 mmol) was added dropwise. After stirring the mixture for 15 minutes, methanol was added thereto. The mixture was heated to 0° C., washed by 1N HCl and an aqueous saturated solution of sodium chloride and dried over magnesium sulfate. The solvent was distilled off to obtain the title compound ( 10.8 g) having the following physical data.

TLC: Rf 0.64 (ethyl acetate:hexane=2:1); NMR (CDCl$_3$): δ 7.4–7.1 (m, 4H), 4.43 (s, 2H), 4.25–3.95 (m, 3H), 3.41 (s, 3H), 2.9–2.8 (m, 2H), 2.12 (s, 3H).

REFERENCE EXAMPLE 5

(2S)-3-(3-Methoxymethylphenyl)-1-acetyloxy-2-(2-tetrahydropyranyloxy)propane

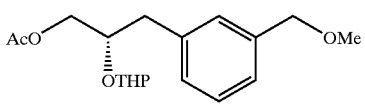

To a solution of a compound prepared in Reference Example 4 (10.8 g) in methylene chloride (40 ml), dihydropyran (5.5 ml, 60 mmol) and pyridinium p-toluenesulfonate (0.50 g) were added. The mixture was stirred for 4 hours, concentrated, diluted with ethyl acetate, washed by water and an aqueous saturated solution of sodium hydrogencarbonate and dried over sodium sulfate. The solvent was distilled off. The residue was purified with a silica gel column chromatography to obtain the title compound (14.0 g) having the following physical data.

TLC: Rf 0.53 (ethyl acetate:hexane:methylene chloride= 1:2:2); NMR (CDCl$_3$): δ 7.3–7.1 (m, 4H), 4.85–4.8 and 4.45–4.0 (m, 1H), 4.43 (s, 2H), 4.25–3.85 and 3.5–3.2 (m, 5H), 3.39 (s, 3H), 3.05–2.8 (m, 2H), 2.10 and 2.08 (s, 3H), 1.9–1.4 (m, 6H).

REFERENCE EXAMPLE 6

(2S)-3-(3-Methoxymethylphenyl)-2-(2-tetrahydropyranyloxy)propan-1-ol

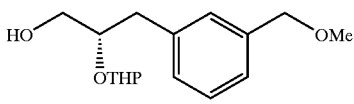

To a solution of a compound prepared in Reference Example 5 (14.0 g) in methanol (40 ml), an aqueous solution of 2N sodium hydroxide (5 ml) was added. The mixture was stirred for 1 hour at room temperature. The solvent was distilled off under reduced pressure. The reaction mixture was diluted with ether, washed by water and an aqueous saturated solution of sodium chloride, dried over magnesium sulfate and concentrated. The residual oil compound was purified with a silica gel column chromatography to obtain the title compound (11.0 g) having the following physical data.

TLC: Rf 0.51, 0.41 (diastereomer mixtures of THP compound, ethyl acetate:hexane=2:1); NMR (CDCl$_3$): δ 7.3–7.1 (m, 4H), 4.85–4.8 and 4.25–4.2 (m, 1H), 4.42 (s, 2H), 4.05–3.4 (m, 5H), 3.38 (s, 3H), 3.06 (dd, J=14, 6Hz, 1H), 2.85 (dd, J=8 Hz, 1H), 2.8–2.7 and 2.15–2.05 (m, 1H), 1.9–1.4 (m, 6H).

REFERENCE EXAMPLE 7

(2S)-3-(3-Methoxymethylphenyl)-2-(2-tetrahydropyranyloxy)propan-1-al

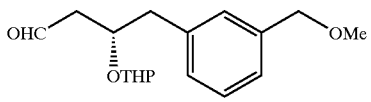

A solution of oxalyl chloride (6.8 ml, 78 mmol) in methylene chloride (150 ml) was cooled to −78° C. Thereto, a solution of anhydrous dimethylsulfoxide (DMSO) (11.1 ml, 156 mmol) in methylene chloride (30 ml) was added dropwise for 15 minutes. After stirring the mixture for 15 minutes, a solution of a compound prepared in Reference Example 6 (11.0 g, 39 mmol) in methylene chloride (40 ml) was added dropwise for 35 minutes. After stirring the mixture for 10 minutes, triethylamine (32 ml) was added thereto. The mixture was heated to −40° C., stirred for 45 minutes, poured into 1N HCl and extracted with mixture solution of ether-hexane. The organic layer was washed by water, an aqueous saturated solution of sodium hydrogencarbonate and an aqueous saturated solution of sodium chloride sucessively and dried over sodium sulfate. The solvent was distilled off to obtain the title compound (11.1 g) having the following physical data.

TLC: Rf 0.45 (ethyl acetate:hexane=1:2); NMR (CDCl$_3$): δ 9.75–9.0 (m, 1H), 7.3–7.1 (m, 4H), 4.8–4.75 and 4.35–4.3 (m, 1H), 4.43 (s, 2H), 4.45–4.3 and 4.1–4.0 (m, 1H), 3.95–3.9 and 3.5–3.4 (m, 1H), 3.40 (s, 3H), 3.3–2.8 (m, 3H), 1.9–1.3 (m, 6H).

REFERENCE EXAMPLE 8

(3S)-1,1-Dibromo-4-(3-methoxymethylphenyl)-3-(2-tetrahydropyranyloxy)-1-buten

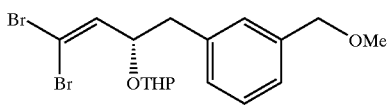

A solution of tetrabromo methane (39.8 g, 0.12 mol) in methylene chloride (150 ml) was cooled to −20° C. Thereto, a solution of triphenylphosphine (63 g, 0.24 mol) in methylene chloride (100 ml) was added dropwise for 20 minutes. The obtained red-brown solution was cooled to −40° C. Thereto, a solution of a compound prepared in Reference Example 7 (11.1 g) and triethylamine (5.6 ml, 40 mmol) in methylene chloride (40 ml) was added dropwise. After stirring the mixture for 10 minutes, triethylamine (11.7 ml) and methanol (9.8 ml) were added thereto. With stirring the obtained brown solution vigorously, the said solution was poured into mixture solution of ether-hexane. The solid product was filtered. The filtrate was concentrated. The residue was purified with a silica gel column chromatography to obtain the title compound (13.6 g) having the following physical data.

TLC: Rf 0.36 (ethyl acetate:hexane=1:9).

REFERENCE EXAMPLE 9

(3S)-4-(3-Methoxymethylphenyl)-3-(2-tetrahydropyranyloxy)-1-butyne

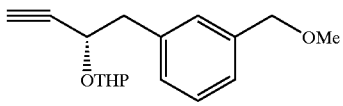

A solution of a compound prepared in Reference Example 8 (13.5 g, 31.1 mmol) in anhydrous THF (90 ml) was cooled to −78° C. Thereto, a solution of n-butyl litium in hexane (1.61M, 42.5 ml, 68.4 mmol) was added dropwise for 20 minutes. After stirring the mixture for 10 minutes, the reaction mixture was poured into an aqueous saturated solution of ammonium chloride and extracted with ethyl acetate. The organic layer was washed by an aqueous saturated solution of sodium chloride and dried over sodium sulfate. The solvent was distilled off. The residue was purified with a silica gel column chromatography to obtain the title compound (8.9 g) having the following physical data.

TLC: Rf 0.50, 0.44 (ethyl acetate:hexane=1:4).

REFERENCE EXAMPLE 10

(3S)-4-(3-Methoxymethylphenyl)-1-butyn-3-ol

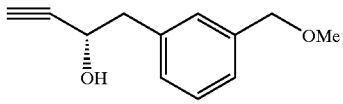

A compound prepared in Reference Example 9 (8.9 g) was dissolved into mixture solvent of dioxane (10 ml) and methanol (10 ml). Thereto, 4N HCl-dioxane (2 ml) was added at room temperature. The mixture was stirred for 1 hour. The reaction mixture was diluted with water and extracted with ethyl acetate. The organic layer was washed by an aqueous saturated solution of sodium hydrogencarbonate and an aqueous saturated solution of sodium chloride successively, and dried over sodium sulfate. The solvent was distilled off. The residue was purified with a silica gel column chromatography to obtain the title compound (5.6 g) having the following physical data.

TLC: Rf 0.40 (ethyl acetate:hexane=1:2).

REFERENCE EXAMPLE 11

(3S)-4-(3-Methoxymethylphenyl)-3-t-butyidimethylsilyloxy-1-butyne

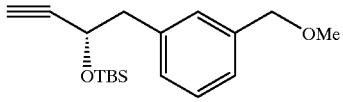

To a solution of a compound prepared in Reference Example 10 (5.64 g, 29 mmol) and imidazole (3.0 g, 44 mmol) in N,N-dimethylformamide (DMF) (30 ml), t-butyidimethylsilyl chloride (5.3 g, 35 mmol) was added. The mixture was stirred overnight at room temperature. The reaction mixture was poured into water and extracted with ethyl acetate. The organic layer was washed by water and an aqueous saturated solution of sodium chloride successively, and dried over sodium sulfate. The solvent was distilled off. The residue was purified with a silica gel column chromatography to obtain the title compound (7.82 g) having the following physical data.

TLC: Rf 0.73 (ethyl acetate:hexane=1:4); NMR (CDCl$_3$): δ 7.3–7.1 (m, 4H), 4.5–4.45 (m, 1H), 4.44 (s, 2H), 3.37 (s, 3H), 3.0–2.95 (m, 2H), 2.41 (d, J=2Hz, 1H), 0.83 (s, 9H), −0.02 (s, 3H), −0.08 (s, 3H).

REFERENCE EXAMPLE 12

(3S)-1-Iodo-4-(3-methoxymethylphenyl)-3-t-butyldimethylsilyloxy-1E-buten

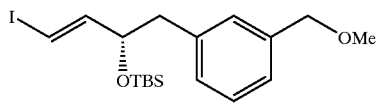

To a suspension of zirconocene chloride hydride (7.81 g, 30 mmol) in anhydrous THF (15 ml), a solution of a compound prepared in Reference Example 11 (7.7 g, 25 mmol) in THF (30 ml) was added dropwise at room temperature. After stirring the mixture for 45 minutes, the mixture was cooled to 0° C. Thereto, a solution of iodide (6.43 g, 25 mmol) in THF was added dropwise. The mixture was stirred for 15 minutes at room temperature. Thereto, hexane was added. The precipitate was filtered by silica gel. The filtrate was concentrated. The residue was purified with a silica gel column chromatography to obtain the title compound (9.77 g) having the following physical data.

TLC: Rf 0.61 (ethyl acetate:hexane=1:9); NMR (CDCl$_3$): δ 7.3–7.05 (m, 4H), 6.56 (dd, J=15, 5 Hz, 1H), 6.19 (dd, J=15, 1 Hz, 1H), 4.43 (s, 2H), 4.3–4.15 (m, 1H), 3.38 (s, 3H), 2.8–2.7 (m, 2H), 0.83 (s, 9H), −0.08 (s, 3H), −0.11 (s, 3H).

REFERENCE EXAMPLE 13

(11α,13E,15α)-7-Hydroxy-9-oxo-11,15-bis(t-butyldimethylsilyloxy)-16-(3-methoxymethylphenyl)-17,18,19,20-tetranor-5-thiaprost-13-enoic Acid·Methyl Ester

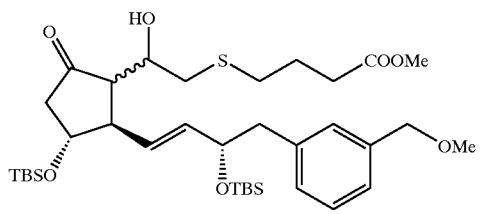

Under atmosphere of argon gas, to a solution of a compound prepared in Reference Example 12 (432 mg) in anhydrous diethyl ether (5 ml), a solution of t-butyl lithium in pentane (1.2 ml, 1.64 M) was added dropwise at −78° C. The mixture was stirred for 1 hour. To the reaction mixture, a solution of lithium 2-thienylcyanocuprite in THF (4.8 ml, 0.25 M) was added dropwise. The mixture was stirred for 30 minutes. Thereto, a solution of (4R)-4-t-butyldimethylsilyloxy-2-cyclopentenone (150 mg) in anhydrous THF (1 ml) was added dropwise slowly. The mixture was stirred for 30 minutes. After cooling the mixture to −78° C., to the reaction mixture, a solution of 2-(3- methoxycarbonylpropylthio)ethanol (150 mg, prepared according to the method described in Chem. Pharm. Bull., 33 (5), 1815–1825 (1985)) in anhydrous THF (1 ml) was added dropwise. The mixture was stirred for 20 minutes. Thereto, an aqueous saturated solution of ammonium chloride was added at −78° C. The mixture was heated to 0° C. The reaction mixture was extracted with hexane. The extract was washed by mixture solvent (an aqueous saturated solution of ammonium chloride:28% ammonium water=4:1) and an aqueous saturated solution of sodium chloride successively, dried over sodium sulfate and concentrated. The residue was purified with a silica gel column chromatography (hexane:ethyl acetate=10:1→6:1) to obtain the title compound (415 mg) having the following physical data.

TLC: Rf 0.36 (hexane:ethyl acetate=4:1); NMR (CDCl₃): δ 7.3–7.05 (m, 4H), 5.68 (dd, J=16, 5 Hz, 1H), 5.50 (dd, J=16, 5 Hz, 1H), 4.43 (s, 2H), 4.35–4.2 (m, 1H), 4.15–4.0 (m, 1H), 3.75–3.65 (m, 1H), 3.67 (s, 3H), 3.40 (s, 3H), 2.9–2.7 (m, 5H), 2.65–2.5 (m, 3H), 2.43 (t, J=7 Hz, 2H), 2.35–2.2 (m, 2H), 2.0–1.8 (m, 2H), 0.90 (s, 9H), 0.85 (s, 9H), 0.10 (s, 3H), 0.08 (s, 3H), −0.10 (s, 3H), −0.22 (s, 3H).

REFERENCE EXAMPLE 14

(11α,13E,15α)-9-oxo-11,15-bis(t-Butyldimethylsilyloxy)-16-(3-methoxymethylphenyl)-17,18,19,20-tetranor-5-thiaprost-7,13-dienoic Acid·Methyl Ester

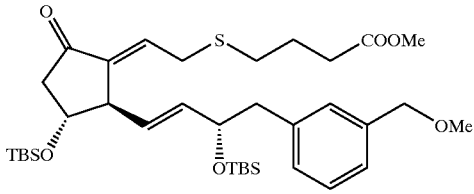

To a solution of a compound prepared in Reference Example 13 (415 mg) in methylene chloride (4 ml), N,N-dimethylaminopyridine (440 mg) and methanesulfonyl chloride (186 μl) were added at 0° C. The mixture was stirred for 2 hours. Thereto, water was added at 0° C. The mixture was extracted with ethyl acetate. The extract was washed by an aqueous saturated solution of sodium hydrogencarbonate, an aqueous saturated solution of potassium hydrogen sulfate and an aqueous saturated solution of sodium chloride successively, dried over anhydrous sodium sulfate and concentrated. The residue was purified with a silica gel column chromatography (hexane:ethyl acetate=10:1) to obtain the title compound (346 mg) having the following physical data.

TLC: Rf 0.48 (hexane:ethyl acetate=4:1); NMR (CDCl₃): δ 7.3–7.0 (m, 4H), 6.8–6.65 (m, 1H), 5.6–5.45 (m, 2H), 4.43 (s, 2H), 4.3–4.2 (m, 1H), 4.15–4.1 (m, 1H), 3.67 (s, 3H), 3.45–3.4 (m, 1H), 3.39 (s, 3H), 3.2–3.05 (m, 2H), 2.8–2.7 (m, 2H), 2.6–2.2 (m, 6H), 2.0–1.8 (m, 2H), 0.85 (s, 9H), 0.83 (s, 9H), 0.08 (s, 3H), 0.06 (s, 3H), −0.12 (s, 3H), −0.22 (s, 3H).

REFERENCE EXAMPLE 15

(11α,13E,15α)-9-oxo-11,15-bis(t-Butyidimethylsilyloxy)-16-(3-methoxymethylphenyl)-17,18,19,20-tetranor-5-thiaprost-13-enoic Acid·Methyl Ester

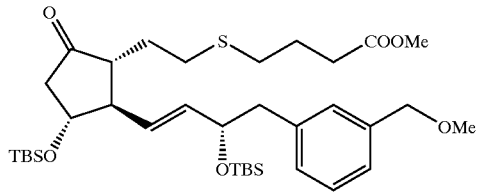

To a solution of a compound prepared in Reference Example 14 (346 mg) in tributyltin hydride (3 ml), t-butylperoxide (90 mg) was added. The mixture was stirred for 35 minutes at 100° C. The reaction mixture was cooled to room temperature and purified with a silica gel column chromatography (hexane:ethyl acetate=100:1→10:1) to obtain the title compound (64 mg) having the following physical data.

TLC: Rf 0.28 (benzene:ethyl acetate=19:1); NMR (CDCl₃): δ 7.3–7.0 (m, 4H), 5.67 (dd, J=15, 6 Hz, 1H), 5.55 (dd, J=15, 8 Hz, 1H), 4.42 (s, 2H), 4.29 (q, J=6 Hz, 1H), 4.05 (q, J=8 Hz, 1H), 3.69 (s, 3H), 3.38 (s, 3H), 2.8–2.7 (m, 2H), 2.7–2.5 (m, 5H), 2.5–2.4 (m, 3H), 2.23 (dd, J=18, 8 Hz, 1H), 2.1–2.0 (m, 1H), 1.9–1.7 (m, 4H), 0.90 (s, 9H), 0.83 (s, 9H), 0.09 (s, 3H), 0.07 (s, 3H), −0.10 (s, 3H), −0.28 (s, 3H).

EXAMPLE 1

(11α,13E,15α)-9-oxo-11,15-Dihydroxy-16-(3-methoxymethylphenyl)-17,18,19,20-tetranor-5-thiaprost-13-enoic Acid·Methyl Ester

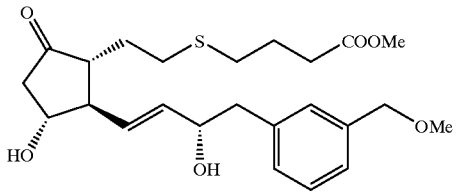

To a solution of a compound prepared in Reference Example 15 (33 mg) in acetonitrile (1.5 ml), pyridine (0.1 ml) and hydrogen fluoride-pyridine complex (0.2 ml) were added at 0° C. The mixture was stirred for 2 hours at room temperature. The reaction mixture was added to the cooled mixture solution (ethyl acetate:an aqueous saturated solution of sodium hydrogencarbonate). The mixture was extracted with ethyl acetate. The extract was washed by an aqueous saturated solution of sodium hydrogencarbonate and an aqueous saturated solution of sodium chloride successively, dried over anhydrous sodium sulfate and concentrated. The residue was purified with a silica gel column chromatography (hexane:ethyl acetate=1:2→1:4→ethyl acetate) to obtain the title compound (16 mg) having the following physical data.

TLC: Rf 0.14 (ethyl acetate); NMR (CDCl₃): δ 7.35–7.1 (m, 4H), 5.75 (dd, J=16, 6 Hz, 1H), 5.52 (dd, J=16, 8 Hz, 1H), 4.42 (s, 2H), 4.4–4.35 (m, 1H), 4.0–3.85 (m, 1H), 3.67 (s, 3H), 3.42 (s, 3H), 3.3–3.2 (m, 1H), 3.0–2.1 (m, 13H), 2.0–1.8 (m, 3H), 1.8–1.6 (m, 1H).

EXAMPLE 1(1)–EXAMPLE 1(11)

By the same procedure described in Reference Example 13, Reference Example 14, Reference Example 15 and Example 1, the following compounds of the present invention were obtained.

EXAMPLE 1(1)

(11α,13E,15α)-9-oxo-11,15-Dihydroxy-16-(3-methyl-4-hydroxyphenyl)-17,18,19,20-tetranor-5-thiaprost-13-enoic Acid·Methyl Ester

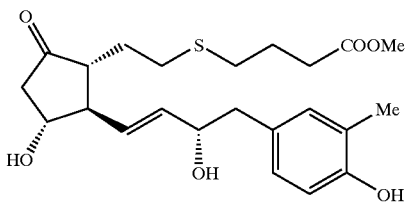

TLC: Rf 0.29 (ethyl acetate); NMR (CDCl$_3$): δ 6.93 (s, 1H), 6.87 (d, J=8 Hz, 1H), 6.71 (d, J=8 Hz, 1H), 5.71 (dd, J=15, 7 Hz, 1H), 5.62 (s, 1H), 5.50 (dd, J=15, 8 Hz, 1H), 4.4–4.2 (m, 1H), 4.1–3.9 (m, 1H), 3.68 (s, 3H), 3.35–3.3 (br, 1H), 2.8–2.6 (m, 3H), 2.6–2.4 (m, 7H), 2.4–2.1 (m, 3H), 2.22 (s, 3H), 2.0–1.8 (m, 3H), 1.7–1.5 (m, 1H

EXAMPLE 1(2)

(11α,13E,15α)-9-oxo-11,15-Dihydroxy-16-(3-methoxymethylphenyl)-17,18,19,20-tetranor-5-thiaprost-13-enoic Acid·Ethyl Ester

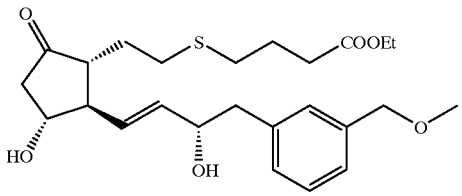

TLC: Rf 0.31 (ethyl acetate:acetic acid=50:1); NMR (300 MHz, CDCl$_3$): δ 7.33–7.10 (m, 4H), 5.74 (dd, J=15, 6.2 Hz, 1H), 5.53 (ddd, J=15, 8.5, 1.1 Hz, 1H), 4.48–4.36 (m, 3H), 4.12 (q, J=7.2 Hz, 2H), 3.94 (m, 1H), 3.41 (s, 3H), 2.89 (dd, J=14, 5.4 Hz, 1H), 2.83 (dd, J=14, 6.9 Hz, 1H), 2.69 (ddd, J=19, 7.6, 1.1 Hz, 1H), 2.65–2.50 (m, 2H), 2.49 (t, J=7.2 Hz, 2H), 2.40 (t, J=7.4 Hz, 2H), 2.38–2.13 (m, 3H), 1.96–1.82 (m, 3H), 1.76–1.61 (m, 1H), 1.25 (t, J=7.2 Hz, 3H).

EXAMPLE 1(3)

(11α,13E,15α)-9-oxo-11,15-Dihydroxy-16-(3-methoxymethylphenyl)-17,18,19,20-tetranor-5-thiaprost-13-enoic Acid·n-Propyl Ester

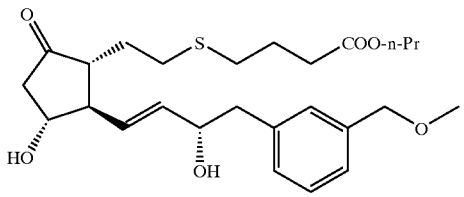

TLC: Rf 0.39 (ethyl acetate:acetic acid=50:1); NMR (300 MHz, CDCl$_3$): δ 7.33–7.09 (m, 4H), 5.74 (dd, J=15, 6.0 Hz, 1H), 5.54 (ddd, J=15, 8.4, 0.9 Hz, 1H), 4.48–4.36 (m, 3H), 4.02 (t, J=6.8 Hz, 2H), 3.94 (m, 1H), 3.41 (s, 3H), 2.89 (dd, J=14, 5.4 Hz, 1H), 2.83 (dd, J=14, 6.9 Hz, 1H), 2.69 (ddd, J=19, 7.5, 1.0 Hz, 1H), 2.66–2.51 (m, 2H), 2.50 (t, J=7.2 Hz, 2H), 2.42 (t, J=7.4 Hz, 2H), 2.38–2.14 (m, 3H), 1.95–1.81 (m, 3H), 1.74–1.57 (m, 3H), 0.93 (t, J=7.4 Hz, 3H).

EXAMPLE 1(4)

(11α,13E,15α)-9-oxo-11,15-Dihydroxy-16-(3-methoxymethylphenyl)-17,18,19,20-tetranor-5-thiaprost-13-enoic Acid·i-Propyl Ester

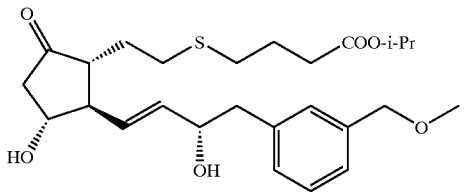

TLC: Rf 0.35 (ethyl acetate:acetic acid=50:1); NMR (300 MHz, CDCl$_3$): δ 7.33–7.11 (m, 4H), 5.74 (dd, J=15, 5.7 Hz, 1H), 5.54 (dd, J=15, 8.4 Hz, 1H), 4.99 (septet, J=6.3 Hz, 1H), 4.48–4.37 (m, 3H), 3.94 (m, 1H), 3.42 (s, 3H), 2.90 (dd, J=14, 5.6 Hz, 1H), 2.83 (dd, J=14, 7.1 Hz, 1H), 2.69 (dd, J=19, 7.4 Hz, 1H), 2.63–2.52 (m, 2H), 2.49 (t, J=7.4 Hz, 2H), 2.37 (t, J=7.4 Hz, 2H), 2.36–2.13 (m, 3H), 1.96–1.81 (m, 3H), 1.74(m, 1H), 1.22 (d, J=6.3 Hz, 6H).

EXAMPLE 1(5)

(11α,13E,15α)-9-oxo-11,15-Dihydroxy-16-(3-methoxymethylphenyl)-17,18,19,20-tetranor-5-thiaprost-13-enoic Acid·n-Butyl Ester

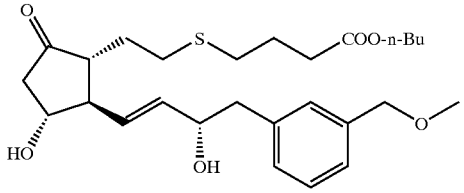

TLC: Rf 0.36 (ethyl acetate:acetic acid=50:1); NMR (300 MHz, CDCl$_3$): δ 7.33–7.11 (m, 4H), 5.75 (dd, J=16, 6.2 Hz, 1H), 5.54 (dd, J=16, 8.5 Hz, 1H), 4.48–4.36 (m, 3H), 4.07

(t, J=6.6 Hz, 2H), 3.94 (m, 1H), 3.42 (s, 3H), 2.90 (dd, J=13, 5.6 Hz, 1H), 2.84 (dd, J=13, 6.9 Hz, 1H), 2.69 (dd, J=19, 7.5 Hz, 1H), 2.64–2.52 (m, 2H), 2.50 (t, J=7.2 Hz, 2H), 2.41 (t, J=7.2 Hz, 2H), 2.38–2.14 (m, 3H), 1.96–1.81 (m, 3H), 1.74–1.53 (m, 3H), 1.43–1.30 (m, 2H), 0.93 (t, J=7.4 Hz, 3H).

EXAMPLE 1(6)

(11α,13E,15α)-9-oxo-11,15-Dihydroxy-16-(3-ethoxymethylphenyl)-17,18,19,20-tetranor-5-thiaprost-13-enoic Acid·Methyl Ester

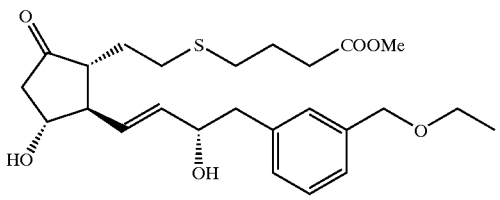

TLC: Rf 0.29 (ethyl acetate); NMR (300 MHz, CDCl₃): δ 7.32–7.12 (m, 4H), 5.77 (dd, J=15.3, 5.4 Hz, 1H), 5.53 (dd, J=15.3, 7.8 Hz, 1H), 4.48–4.43 (m, 3H), 3.97–3.87 (m, 1H), 3.67 (s, 3H), 3.58 (q, J=6.9 Hz, 2H), 2.98–2.80 (m, 2H), 2.76–2.14 (m, 13H), 1.95–1.60 (m, 3H), 1.26 (t, J=7.2 Hz, 3H).

EXAMPLE 1(7)

(11α, 13E,15α)-9-oxo-11,15-Dihydroxy-16-(3-n-propyloxymethylphenyl)-17,18,19,20-tetranor-5-thiaprost-13-enoic Acid·Methyl Ester

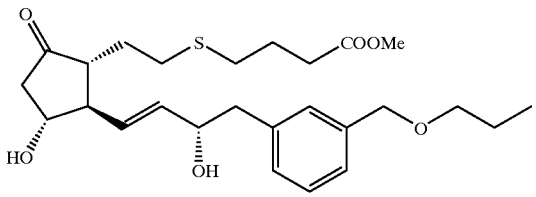

TLC: Rf 0.36 (ethyl acetate); NMR (300 MHz, CDCl₃): δ 7.32–7.13 (m, 4H), 5.77 (dd, J=15.3, 6.0 Hz, 1H), 5.53 (dd, J=15.3, 8.0 Hz, 1H), 4.48–4.43 (m, 3H), 3.97–3.89 (m, 1H), 3.67 (s, 3H), 3.47 (t, J=6.6 Hz, 2H), 2.94–2.91 (m, 2H), 2.76–2.14 (m, 13H), 1.92–1.50 (m, 5H), 0.95 (t, J=7.5 Hz, 3H).

EXAMPLE 1(8)

(11α,13E,15α)-9-oxo-11,15-Dihydroxy-16-(3-methoxymethylphenyl)-17,18,19,20-tetranor-5-thiaprost-13-enoic Acid·t-Butyl Ester

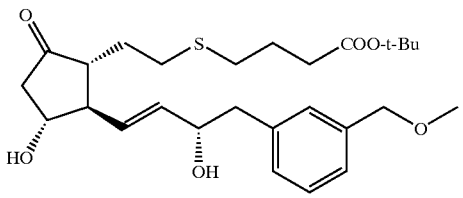

TLC: Rf 0.35 (ethyl acetate); NMR (300 MHz, CDCl₃): δ 7.35–7.16 (m, 4H), 5.78 (dd, J=15.3, 5.1 Hz, 1H), 5.54 (dd, J 15.3, 7.5 Hz, 1H), 4.50–4.40 (m, 3H), 4.00–3.92 (m, 1H), 3.42 (s, 3H), 2.97–2.82 (m, 2H), 2.76–2.15 (m, 11H), 1.95–1.63 (m, 3H), 1.44 (s, 9H).

EXAMPLE 1(9)

(11α,15α, 13E)-9-oxo-11,15-Dihydroxy-16-methyl-16-(3-methoxymethylphenyl)-17,18,19,20-tetranor-5-thiaprost-13-enoic Acid·Methyl Ester

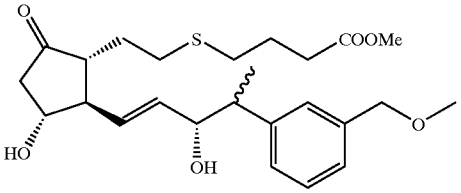

TLC: Rf 0.40 (ethyl acetate); NMR (300 MHz, CDCl₃): δ 7.36–7.11 (m, 4H), 5.76–5.60 (m, 1H), 5.56–5.42 (m, 1H), 4.48–4.37 (m, 2H), 4.29–4.20 (m, 1H), 3.96–3.75 (m, 1H), 3.67 (s, 3H), 3.43 (s, 3H), 2.96–2.05 (m, 11H), 1.97–1.60 (m, 6H), 1.37 (d, J=8.0 Hz, 1.5H), 1.30 (d, J=7.2 Hz, 1.5H).

EXAMPLE 1(10)

(15α,13E)-9-oxo-15-Hydroxy-16-(3-methoxymethylphenyl)-17,18,19,20-tetranor-5-thiaprost-13-enoic Acid·Methyl Ester

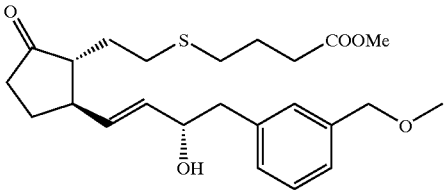

TLC: Rf 0.60 (ethyl acetate:hexane=2:1); NMR (300 MHz, CDCl₃): δ 7.3–7.1 (m, 4H), 5.7–5.6 (m, 2H), 4.44 (s, 2H), 4.4–4.3 (br, 1H), 3.68 (s, 3H), 3.41 (s, 3H), 2.9–2.75 (m, 2H), 2.7–2.3 (m, 8H), 2.3–2.0 (m, 3H), 2.0–1.5 (m, 6H).

EXAMPLE 1(11)

(11α,15α,13E)-9-oxo-11,15-Dihydroxy-16-(3-methyl4-hydroxyphenyl)-17,18,19,20-tetranor-5-thiaprost-13-enoic Acid·Methyl Ester

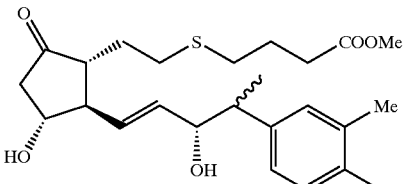

TLC: Rf 0.45 (ethyl acetate); NMR (300 MHz, CDCl₃): δ 6.99–6.82 (m, 2H), 6.75–6.68 (m, 1H), 5.73–5.54 and 5.44–5.31 (m, 3H), 4.14–3.90 (m, 2H), 3.70 (s, 3H), 2.82–2.06 (m, 14H), 1.99–1.53 (m, 6H), 1.31 and 1.20 (d, J=7.0 Hz, 3H).

REFERENCE EXAMPLE 16

(9α,11α,13E,15α)-9-Hydroxy-11,15-bis(t-butyldimethylsilyloxy)-16-(3-methoxymethylphenyl)-17,18,19,20-tetranor-5-thiaprost-13-enoic Acid·Methyl Ester

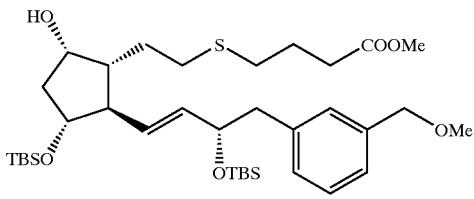

Under an atmosphere of argon gas, to a solution of a compound prepared in Reference Example 15 (186 mg) in anhydrous THF (3 ml), a solution of lithium tri-s-butylcyano hydride in THF (320 µl, 1.0 M) was added dropwise at −78° C. The mixture was stirred for 1 hour. After adding 1N HCl to the reaction mixture, the mixture was heated to 0° C. and extracted with ethyl acetate. The extract was washed by water and an aqueous saturated solution of sodium chloride successively, dried over anhydrous sodium sulfate and concentrated. The residue was purified with a silica gel column chromatography (hexane:ethyl acetate=6:1→4:1) to obtain the title compound (77mg) having the following physical data.

TLC: Rf 0.26 (hexane:ethyl acetate=4:1); NMR (CDCl$_3$): δ 7.3–7.0 (m, 4H), 5.51 (dd, J=15, 6 Hz, 1H), 5.35 (dd, J=15, 8 Hz, 1H), 4.42 (s, 2H), 4.22 (q, J=6 Hz, 1H), 4.2–4.1 (m, 1H), 4.1–3.95 (m, 1H), 3.69 (s, 3H), 3.38 (s, 3H), 2.8–2.7 (m, 3H), 2.7–2.4 (m, 6H), 2.3–2.15 (m, 1H), 2.0–1.8 (m, 5H), 1.7–1.5 (m, 2H), 0.88 (s, 9H), 0.82 (s, 9H), 0.08 (s, 6H), −0.10 (s, 3H), −0.22 (s, 3H).

EXAMPLE 2

(9β,11α,13E,15α)-9-Chloro-11,15-dihydroxy-16-(3-methoxymethylphenyl)-17,18,19,20-tetranor-5-thiaprost-13-enoic Acid·Methyl Ester

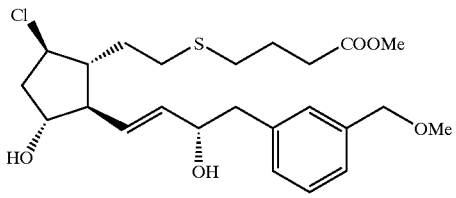

1) Under an atmosphere of argon gas, to a solution of a compound prepared in Reference Example 16 (95 mg) in anhydrous pyridine (1.5 ml), After stirring the mixture, ethyl acetate was added thereto. The reaction mixture was washed by 1N HCl, an aqueous saturated solution of sodium hydrogencarbonate and an aqueous saturated solution of sodium chloride successively, dried over anhydrous sodium sulfate and concentrated. The obtained tosyl compound was used for the next reaction without purification.

2) Under an atmosphere of argon gas, to a solution of the obtained tosyl compound in anhydrous toluene (6 ml), tetra-n-butylammonium chloride (390 mg) was added rapidly. The mixture was stirred for 1 hour at 55° C. The reaction mixture was dilluted with ethyl acetate, washed by water and an aqueous saturated solution of sodium chloride successively, dried over anhydrous magnesium sulfate and concentrated. The obtained crude product was used for the next reaction without purification.

3) To a solution of the obtained crude product in acetonitrile ( 3 ml), pyridine (0.2 ml) and hydrogen fluoride-pyridine complex (0.4 ml) were added at 0° C. The mixture was stirred for 1 hour at room temperature. The reaction mixture was added to a mixture solution (ethyl acetate-an aqueous saturated solution of sodium hydrogencarbonate) and extracted with ethyl acetate. The extract was washed by an aqueous saturated solution of sodium hydrogencarbonate and an aqueous saturated solution of sodium chloride successively, dried over anhydrous sodium sulfate and concentrated. The residue was purified with a short column and then with silica gel column chromatography (toluene:i-propanol=50:1) to obtain the title compound (38 mg) having the following physical data.

TLC: Rf 0.42 (ethyl acetate); NMR (CDCl$_3$): δ 7.3–7.1 (m, 4H), 5.63 (dd, J=15, 6 Hz, 1H), 5.48 (dd, J=15, 8 Hz, 1H), 4.42 (s, 2H), 4.4–4.3 (m, 1H), 4.1–3.9 (m, 2H), 3.68 (s, 3H), 3.42 (s, 3H), 3.0–2.7 (m, 3H), 2.6–2.4 (m, 6H), 2.35–2.1 (m, 3H), 2.1–1.8 (m, 4H), 1.8–1.6 (m, 2H).

EXAMPLE 2(1)

(9β,11α,13E,15α)-9-Fluoro-11,15-dihydroxy-16-(3-methoxymethylphenyl)-17,18,19,20-tetranor-5-thiaprost-13-enoic Acid·Methyl Ester

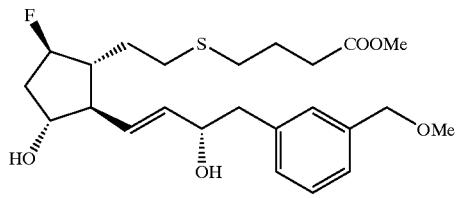

By the same procedure described in Reference Example 16 and Example 2, the title compound was obtained. TLC: Rf 0.49 (hexane:ethyl acetate=1:3); NMR (CDCl$_3$): δ 7.3–7.1 (m, 4H), 5.66 (dd, J=15, 6 Hz, 1H), 5.49 (dd, J=15, 8 Hz, 1H), 4.85–4.8 and 4.7–4.65 (m, 1H), 4.42 (s, 2H), 4.45–4.35 (m, 1H), 4.05–3.9 (m, 1H), 3.68 (s, 3H), 3.42 (s, 3H), 2.95–2.8 (m, 2H), 2.7–2.4 (m, 7H), 2.4–2.2 (m, 1H), 2.1–1.5 (m, 8H).

EXAMPLE 3

(11α,13E,15α)-9-oxo-11,15-Dihydroxy-16-(3-methoxymethylphenyl)-17,18,19,20-tetranor-5-thiaprost-13-enoic Acid

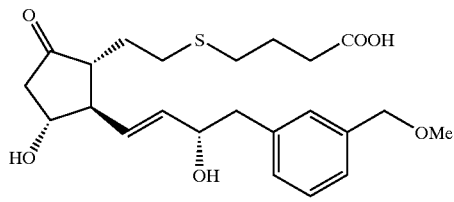

To a solution of a compound prepared in Example 1(16 mg) in dimethylsulfoxide (1 ml), phosphate buffer (1 ml, pH7.4) and then pig liver esterase (100 µl) were added. The mixture was stirred for 2 hours at room temperature. The reaction mixture was acidified by addition of an aqueous saturated solution of ammonium sulfate and 1N HCl. The mixture was extracted with ethyl acetate. The extract was washed by water and an aqueous saturated solution of sodium chloride successively, dried over anhydrous sodium sulfate and concentrated. The residue was purified with a silica gel column chromatography (hexane:ethyl acetate=1:2, 1% acetic acid→1:4, 1% acetic acid→ethyl acetate:acetic acid=50:1) to obtain the title itle compound (13 mg) having the following physical data. TLC: Rf 0.21 (ethyl acetate:acetic acid=19:1); NMR (CDCl₃): δ 7.35–7.1 (m, 4H), 5.76 (dd, J=15, 6 Hz, 1H), 5.53 (dd, J=15, 8 Hz, 1H), 5.2–4.4 (br, 3H), 4.43 (s, 2H), 4.5–4.4 (m, 1H), 3.94 (q, J=8 Hz, 1H), 3.42 (s, 3H), 3.0–2.15 (m, 13H), 2.0–1.8 (m, 2H), 1.8–1.6 (m, 1H).

EXAMPLE 3(1)~EXAMPLE 3(8)

By the same procedure described in Example 3 using compounds prepared in Examples 1(2)~1(8), Examples 2, 2(1), the following compounds were obtained

EXAMPLE 3(1)

(11α,13E,15α)-9-oxo-11,15-Dihydroxy-16-(3-methyl-4-hydroxyphenyl)-17,18,19,20-tetranor-5-thiaprost-13-enoic Acid

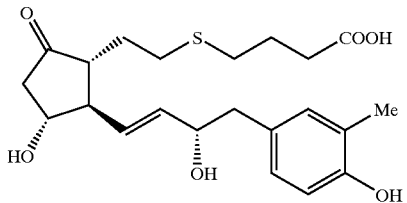

TLC: Rf 0.22 (chloroform:methanol=9:1); NMR (CD₃OD): δ 6.89 (s, 1H), 6.82 (d, J=8 Hz, 1H), 6.63 (d, J=8 Hz, 1H), 5.64 (dd, J=15, 7 Hz, 1H), 5.48 (dd, J=15, 8 Hz, 1H), 4.22 (q, J=7 Hz, 1H), 3.99 (q, J=8 Hz, 1H), 2.9–2.1 (m, 13H), 2.15 (s, 3H), 1.9–1.6 (m, 3H).

EXAMPLE 3(2)

(9β,11α,13E,15α)-9-Chloro-11,15-dihydroxy-16-(3-methoxymethylphenyl)-17,18,19,20-tetranor-5-thiaprost-13-enoic Acid

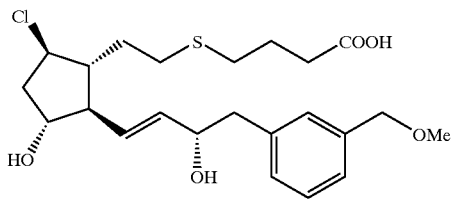

TLC: Rf 0.29 (chloroform:methanol=9:1); NMR (CDCl₃): δ 7.25–7.05 (m, 4H), 5.62 (dd, J=15, 6 Hz, 1H), 5.45 (dd, J=15, 8 Hz, 1H), 4.38 (s, 2H), 4.4–4.3 (m, 1H), 4.0–3.9 (m, 2H), 3.37 (s, 3H), 2.85 (dd, J=14, 5 Hz, 1H), 2.75 (dd, J=14, 7 Hz, 1H), 2.6–2.3 (m, 6H), 2.25–2.05 (m, 2H), 2.0–1.9 (m, 2H), 1.9–1.8 (m, 2H), 1.7–1.6 (m, 2H).

EXAMPLE 3(3)

(9β,11α,13E,15α)-9-Fluoro-11,15-dihydroxy-16-(3-methoxymethylphenyl)-17,18,19,20-tetranor-5-thiaprost-13-enoic Acid

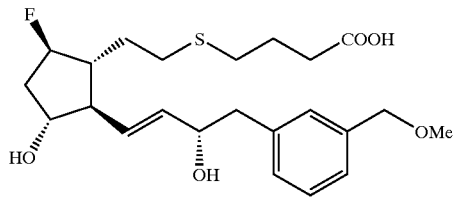

TLC: Rf 0.51(chloroform:methanol=9:1); NMR (CDCl₃): δ 7.3–7.1 (m, 4H), 5.68 (dd, J=15, 6 Hz, 1H), 5.51 (dd, J=15, 9 Hz, 1H), 4.9–4.6 (m, 1H), 4.44 (s, 2H), 4.42 (q, J=6 Hz, 1H), 3.96 (q, J=9 Hz), 1H), 3.42 (s, 3H), 3.8–2.6 (br, 3H), 2.90 (dd, J=14, 6 Hz, 1H), 2.82 (dd, J=14, 6 Hz, 1H), 2.65–2.2 (m, 7H), 2.1–1.5 (m, 7H).

EXAMPLE 3(4)

(11α,13E,15α)-9-oxo-11,15-Dihydroxy-16-(3-ethoxymethylphenyl)-17,18,19,20-tetranor-5-thiaprost-13-enoic Acid

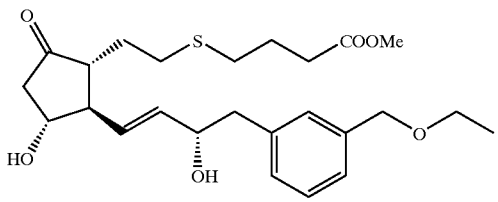

TLC: Rf 0.06 (chloroform:methanol=9:1); NMR (300 MHz, CDCl₃): δ 7.29–7.11 (m, 4H), 5.76 (dd, J=15.0, 5.4 Hz, 1H), 5.53 (dd, J=15.0, 8.1 Hz, 1H), 4.51–4.40 (m, 3H), 3.98–3.90 (m, 1H), 3.59 (q, J=6.9 Hz, 2H), 2.95–2.80 (m, 2H), 2.76–2.16 (m, 10H), 1.94–1.62 (m, 4H), 1.26 (t, J=7.2 Hz, 3H).

EXAMPLE 3(5)

(11α,13E,15α)-9-oxo-11,15-Dihydroxy-16-(3-n-propyloxymethylphenyl)-17,18,19,20-tetranor-5-thiaprost-13-enoic Acid

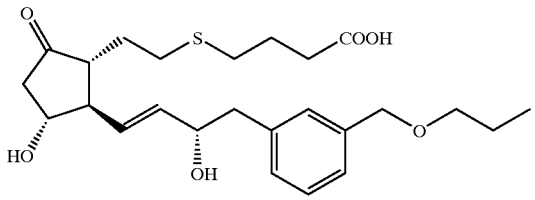

TLC: Rf 0.12 (chloroform:methanol=9:1); NMR (300 MHz, CDCl₃): δ 7.31–7.11 (m, 4H), 5.76 (dd, J 15.3, 5.7 Hz, 1H), 5.54 (dd, J=15.3, 8.4 Hz, 1H), 4.60–4.40 (m, 3H), 3.98–3.90 (m, 1H), 3.41 (t, J=6.9 Hz, 2H), 2.95–2.16 (m, 12H), 1.94–1.59 (m, 6H), 0.95 (t, J=7.5 Hz, 3H).

EXAMPLE 3(6)

(11α,15α,13E)-9-oxo-11,15-Dihydroxy-16-methyl-16-(3-methoxymethylphenyl)-17,18,19,20-tetranor-5-thiaprost-13-enoic Acid

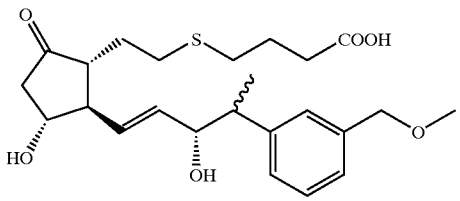

TLC: Rf 0.17 (chloroform:methanol=9:1); NMR (300 MHz, CDCl$_3$): δ 7.36–7.11 (m, 4H), 5.76 and 5.70 (dd, J=15.0, 8.0 Hz, 1H), 5.53 and 5.48 (dd, J=15.0, 6.0 Hz, 1H), 4.50–4.39 (m, 2H), 4.36–4.26 (m, 1H), 3.98–3.75 (m, 1H), 3.44 (s, 3H), 3.02–1.60 (m, 17H), 1.37 and 1.30 (d, J=7.0 Hz, 3H).

EXAMPLE 3(7)

(15α,13E)-9-oxo-15-Hydroxy-16-(3-methoxymethylphenyl)-17,18,19,20-tetranor-5-thiaprost-13-enoic Acid

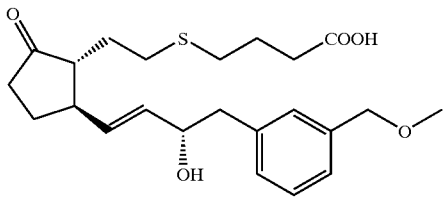

TLC: Rf 0.51 (chloroform:methanol=9:1); NMR (300 MHz, CDCl$_3$): δ 7.3–7.1 (m, 4H), 5.75–5.6 (m, 2H), 4.45 (s, 2H), 4.45–4.4 (m, 1H), 4.0–2.8 (br), 3.42 (s, 3H), 2.89 (dd, J=14, 5 Hz, 1H), 2.79 (dd, J=14, 8 Hz, 1H), 2.7–2.3 (m, 8H), 2.3–2.0 (m, 3H), 2.0–1.5 (m, 5H).

EXAMPLE 3(8)

(11α,15α,13E)-9-oxo-11,15-Dihydroxy-16-(3-methyl-4-hydroxyphenyl)-17,18,19,20-tetranor-5-thiaprost-13-enoic Acid

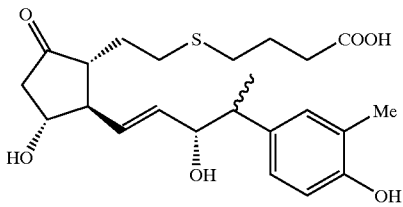

TLC: Rf 0.21 (chloroform methanol=9:1); NMR (300 MHz, CDCl$_3$—CD$_3$OD): δ 7.00–6.67 (m, 3H), 5.75–5.32 (m, 2H), 4.15–3.86 (m, 2H), 3.3 (bs, 3H), 2.80–1.50 (m, 18H), 1.33 and 1.19 (d, J=7.0 Hz, 3H).

REFERENCE EXAMPLE 17

4-Iodobutanoic Acid Methyl Ester

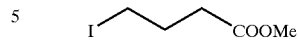

To a solution of methyl 4-chlorobutylate (145.5 g) in acetone (1100 ml), sodium iodide (320 g) was added. The mixture was refluxed with stirring for 11 hours. After reaction, the reaction mixture was cooled to room temperature and filtered by Celite. The filtrate was concentrated under reduced pressure. To the residue, a mixture of ethyl acetate-water (500 ml+500 ml) was added. The mixture was extracted with ethyl acetate.

The organic layer was washed by an aqueous saturated solution of sodium thiosulfate (300 ml) and an aqueous saturated solution of sodium chloride successively and dried over anhydrous magnesium sulfate. The solvent was distilled off under reduced pressure to obtain the title compound (236.5 g).

TLC: Rf 0.36 (hexane:ethyl acetate=9:1); NMR (200 MHz, CDCl$_3$): δ 3.69 (s, 3H), 3.24 (t, J=6.8 Hz, 2H), 2.46 (t, J=7.0 Hz, 2H), 2.13 (tt, J=7.0, 6.8 Hz, 2H).

REFERENCE EXAMPLE 18

3-Bromomethylphenylacetic Acid

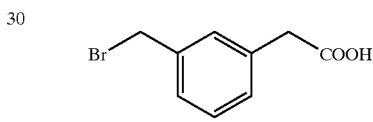

To a solution of 3-methylphenylacetic acid (125 g) in tetrachloro methane (1660 ml), N-bromosuccinimide (148 g) and 2,2'-azobisisobutyronitrile (AIBN; 1.37 g) were added. The mixture was refluxed with heating. After termination of reaction, the solution was cooled with ice. The white precipitate was filtered by glass-filter. The filtrate was washed by tetrachloro methane. The filtrate together with washing liquid was concentrated. The obtained residue was dissolved into ethyl acetate. Thereto, hexane was added. The mixture was crystallized to obtain the title compound (59 g).

TLC: Rf 0.58 (hexane:ethyl acetate=1:1+1% acetic acid); NMR (200 MHz, CDCl$_3$): δ 7.36–7.18 (m, 4H), 4.48 (s, 2H), 3.66 (s, 3H).

REFERENCE EXAMPLE 19

3-Methoxymethylphenylacetic Acid

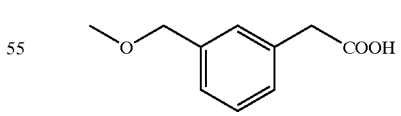

Under an atmosphere of argon gas, to sodium methoxide (160 g), methanol (800 ml) was added with stirring. Thereto, a solution of 3-bromomethylphenylacetic acid (226 g; prepared in Reference Example 18) in methanol (3200 ml) was added. The mixture was refluxed for 20 minutes. After the temperature of mixture became to room temperature, methanol was distilled off. The residue was poured into 2N HCl. Thereto, ethyl acetate was added. The organic layer was washed by an aqueous saturated solution of sodium chloride, dried over anhydrous magnesium sulfate and concentrated to obtain the title compound (176.3 g).

TLC: Rf 0.58 (hexane:ethyl acetate=1:1+1% acetic acid); NMR (200 MHz, CDCl₃): δ 7.38–7.18 (m, 4H), 4.45 (s, 2H), 3.65 (s, 2H), 3.39 (s, 3H).

REFERENCE EXAMPLE 20

N-Methoxy-N-methyl-(3-methoxymethylphenyl) acetic Acid Amide

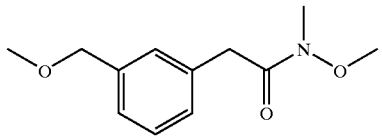

Under an atmosphere of argon gas, to a solution of 3-methoxymethylphenylacetic acid (176.1 g; prepared in Reference Example 19) in methylene chloride (2500 ml), methylmethoxyamine·hydrochloride (289 g), 1-hydroxybenzotriazole (HOBt) monohydrate (166 g) and 1-ethyl-3-[3-(dimethylamino)propyl]carbodiimide monohydrochloride (EDC; 284 mg) were added successively. Thereto, N-methylmorpholin (325 ml) was added. The mixture was stirred at room temperature.

After 11 hours, to the mixture, EDC monohydrochloride (94.7 g) and N-methylmorpholin (54.0 ml) were added. In addition, the mixture was stirred for 2 hours. The reaction mixture was filtered. The solvent was distilled off under reduced pressure. Thereto, water (600 ml) and ethyl acetate (600 ml) were added. After they were dissolved entirely, the mixture was poured into 2N HCl (2000 ml). This mixture was filtered to remove hydrochloride. The filtrate was separated. The organic layer was washed by 2N HCl, water, an aqueous saturated solution of sodium hydrogencarbonate and an aqueous saturated solution of sodium chloride successively and concentrated under reduced pressure to obtain the title compound (crude product; 200 g).

TLC: Rf 0.58 (ethyl acetate); NMR (200 MHz, CDCl₃): δ 7.36–7.18 (m, 4H), 4.44 (s, 2H), 3.78 (s, 2H), 3.61 (s, 3H), 3.38 (s, 3H), 3.20 (s, 3H).

REFERENCE EXAMPLE 21

Dimethyl 3-(3-Methoxymethylphenyl)-2-oxopropylphosphonate

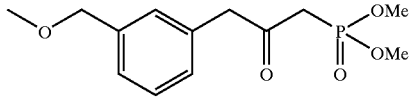

Under an atmosphere of argon gas, a solution of dimethyl methylphosphonate (DMMP; 147 g) in anhydrous toluene (1500 ml) was cooled to −74° C. Thereto, n-butyllithium (714 ml; 1.52 M in hexane) was added for 1 hour. The mixture was stirred for 1 hour. Thereto, a solution of N-methoxy-N-methyl-(3-methoxymethylphenyl)acetic acid amide (200 g; prepared in Reference Example 20) in anhydrous toluene (400 ml) was added for 30 minutes. In addition, the mixture was stirred for 2 hours. Thereto, acetic acid (73.5 ml) was added. The mixture was heated to room temperature and poured into water. The organic layer was separated. The organic layer was washed by water and an aqueous saturated solution of sodium chloride successively, dried over anhydrous magnesium sulfate and concentrated under reduced pressure. The residue was purified with silica gel column chromatography to obtain the title compound (206.5 g).

TLC: Rf 0.22 (ethyl acetate); NMR (200 MHz, CDCl₃): δ 7.38–7.11 (m, 4H), 4.45 (s, 2H), 3.90 (s, 2H), 3.82 (s, 3H), 3.77 (s, 3H), 3.40 (s, 3H), 3.11 (d, J=23 Hz, 2H).

REFERENCE EXAMPLE 22

(1S,5R,6S,7R)-3-oxo-6-Formyl-7-(2-tetrahydropyranyloxy)-2-oxabicyclo[3.3.0]octane

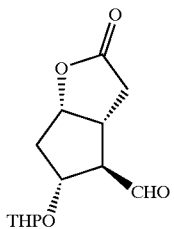

To a solution of (1S,5R,6R,7R)-3-oxo-6-hydroxymethyl-7-(2-tetrahydropyranyloxy)-2-oxabicyclo[3.3.0]octane (140.5 g; J. Am. Chem. Soc., 98, 1490 (1971)) in ethyl acetate (4100 ml), water (410 ml), sodium acetate (134.9 g), potassium bromide (6.53 g) and 2,2,6,6-tetramethyl-1-piperidinyloxyradical (TEMPO; 2.14 g) were added. The mixture was cooled with sodium chloride-water. The reaction mixture was stirred vigorously. Thereto, a solution of 10% sodium hypochlorous acid (302 ml) which was saturated with sodium hydrogencarbonate was added at a dropwise for 40 minutes. After reaction, the organic layer was washed by an aqueous saturated solution of sodium chloride, dried over anhydrous magnesium sulfate and concentrated under reduced pressure to obtain the title compound (113.6 g).

TLC: Rf 0.60 (ethyl acetate:acetic acid=100:1); NMR (300 MHz, CDCl₃): δ 9.73 (m, 1H), 5.11–5.00 (m, 1H), 4.81–4.51 (m, 2H), 3.92–3.79 (m, 1H), 3.59–3.35 (m, 2H), 3.20–3.03 (m, 1H), 2.90 and 2.87 (each dd, J=18, 6.2 Hz and J=18, 6.3 Hz, 1H), 2.57 and 2.44 (each dd, J=18, 3.2 Hz and J=18, 3.2 Hz, 1H), 2.40–2.30 (m, 1H), 1.97–1.42 (m, 7H).

REFERENCE EXAMPLE 23

(1S,5R,6R,7R)-3-oxo-6-(4-(3-Methoxymethylphenyl)-3-oxo-1-butenyl)-7-(2-tetrahydropyranyloxy)-2-oxabicyclo[3.3.0]octane

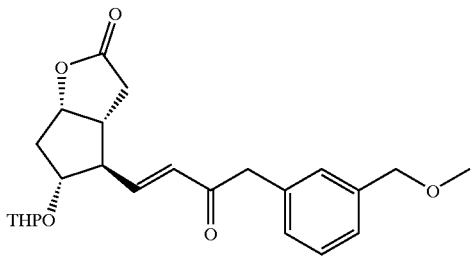

Under an atmosphere of argon gas, a suspension of sodium hydride (5.08 g; 62.5%) in anhydrous THF (2000 ml) was cooled with water bath. Thereto, a solution of dimethyl 3-(3-methoxymethylphenyl)-2-oxopropylphosphonate (42.7 g; prepared in Reference Example 21) in anhydrous THF (1000 ml) was added dropwise for 15 minutes. The mixture was stirred for 1 hour. Thereto, a solution of (1S,5R,6S,7R)-3-oxo-6-formyl-7-(2-tetrahydropyranyloxy)-2-oxabicyclo[3.3.0]octane (113.6 g; prepared in Reference Example 23) in anhydrous THF (800 ml) was added dropwise. The mixture was stirred for 12 hours.

To the reaction mixture, acetic acid (51 ml) was added. The mixture was poured into water. The reaction mixture was extracted with ethyl acetate. The organic layer was washed by an aqueous saturated solution of sodium chloride, dried over anhydrous magnesium sulfate and concentrated under reduced pressure. The residue was purified with silica gel column chromatography (hexane:ethyl acetate=1:1) to obtain the title compound (143.0 g).

TLC: Rf 0.52 (hexane:ethyl acetate=1:1); NMR (200 MHz, CDCl$_3$): δ 7.38–7.07 (m, 4H), 6.71 (m, 1H), 6.22 (m, 1H), 4.97 (m, 1H), 4.68–4.51 (m, 1H), 4.44 (s, 2H), 4.22–3.92 (m, 1H), 3.88–3.34 (m, 2H), 3.81 (s, 2H), 3.40 (s, 3H), 2.88–2.03 (m, 6H), 1.98–1.32 (m, 6H).

REFERENCE EXAMPLE 24

(1S,5R,6R,7R)-3-oxo-6-(4-(3-Methoxymethylphenyl)-3S-hydroxy-1-butenyl)-7-(2-tetrahydropyranyloxy)-2-oxabicyclo[3.3.0]octane

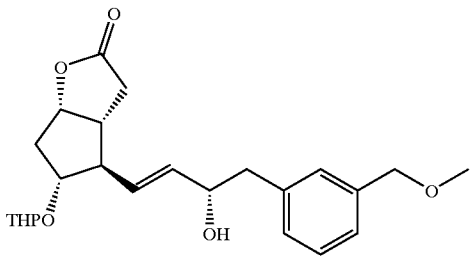

Under an atmosphere of argon gas, to a suspension of lithium aluminum hydride (13.0 g) in anhydrous THF (760 ml), a solution of anhydrous ethanol (15.0 g) in anhydrous THF (90 ml) was added dropwise for 12 minutes. The mixture was stirred for 20 minutes. Thereto, a solution of (S)-binaphthol (93.3 g) in anhydrous THF (200 ml) was added dropwise for 1 hour. The mixture was stirred for 1 hour.

The mixture was cooled to −72° C. Thereto, a solution of (1S,5R,6R,7R)-3-oxo-6-(4-(3-methoxymethylphenyl)-3-oxo-1-butenyl)-7-(2-tetrahydropyranyloxy)-2-oxabicyclo[3.3.0]octane (30.0 g; prepared in Reference Example 23) in anhydrous THF (210 ml) was added dropwise for 30 minutes. The mixture was stirred for 1 hour.

To the reaction mixture, methanol (75 ml) was added dropwise for 10 minutes. The bath was removed. To the mixture, sodium hydrogen tartrate (1500 ml; 0.5 M) was added at −30° C. The mixture was heated to room temperature and extracted with ethyl acetate. The organic layer was washed by an aqueous saturated solution of sodium chloride, dried over anhydrous magnesium sulfate and concentrated under reduced pressure. To the residue, ethyl acetate-hexane (100 ml-230 ml) was added. The mixture was left overnight. The precipitated crystal was filtered. The filtrate was concentrated. The residue was purified with silica gel column chromatography (hexane:ethyl acetate=1:2→ethyl acetate) to obtain the title compound (23.1 g; the title compound:15-epimor=93.9:6.1).

TLC: Rf 0.51 (ethyl acetate); NMR (200 MHz, CDCl$_3$): δ 7.35–7.07 (m, 4H), 5.61 (dd, J=16, 5.5 Hz, 1H), 5.50 and 5.48 (each dd, J=16, 6.5 Hz and J=16, 6.6 Hz, 1H), 4.94 (m, 1H), 4.65 (m, 1H), 4.44 (s, 2H), 4.32 (m, 1H), 4.12–3.38 (m, 3H), 3.41 (s, 3H), 2.87–2.03 (m, 8H), 1.89–1.40 (m, 6H).

REFERENCE EXAMPLE 25

(1S,5R,6R,7R)-3-oxo-6-(4-(3-Methoxymethylphenyl)-3S-(2-tetrahydropyranyloxy)-1-butenyl)-7-(2-tetrahydropyranyloxy)-2-oxabicyclo[3.3.0]octane

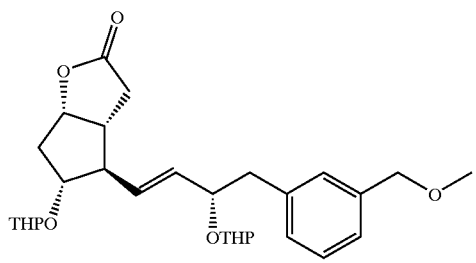

Under an atmosphere of argon gas, to a solution of (1S,5R,6R,7R)-3-oxo-6-(4-(3-methoxymethylphenyl)-3S-hydroxy-1-butenyl)-7-(2-tetrahydropyranyloxy)-2-oxabicyclo[3.3.0]octane (114.7 g; prepared in Reference Example 24) in methylene chloride (1000 ml), dihydropyran (37.7 ml) and tosylic acid monohydrate (524 mg) were added. The mixture was stirred for 1 hour. To the reaction mixture, triethylamine was added at 0° C. The mixture was concentrated under reduced pressure. The residue was purified with silica gel column chromatography (hexane:ethyl acetate=2:1~1:1~1:2) to obtain the title compound (126.9 g).

TLC: Rf 0.51, 0.45 (hexane:ethyl acetate=1:2); NMR (200 MHz, CDCl$_3$): δ 7.32–7.02 (m, 4H), 5.63–5.23 (m, 2H), 4.89 (m, 1H), 4.70–4.46 (m, 1H), 4.42 (s, 2H), 4.35–3.18 (m, 6H), 3.39 (s, 3H), 3.07–1.94 (m, 8H), 1.88–1.20 (m, 12H).

REFERENCE EXAMPLE 26

(9α,11α,15α,13E)-6,9-Dihydroxy-11,15-bis(2-tetrahydropyranyloxy)-16-(3-Methoxymethylphenyl)-1,2,3,4,5,17,18,19,20-nonanorprost-13-en

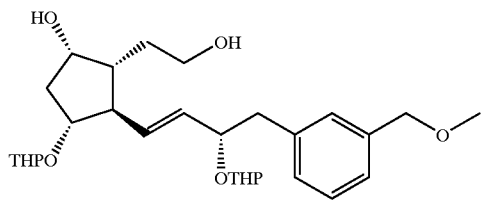

Under an atmosphere of argon gas, lithium aluminum hydride (7.68 g) was cooled with ice. Thereto, anhydrous THF (500 ml) was added. Thereto, a solution of (1S,5R,6R,7R)-3-oxo-6-(4-(3-methoxymethylphenyl)-3S-(2-tetrahydropyranyloxy)-1-butenyl)-7-(2-tetrahydropyranyloxy)-2-oxabicyclo[3.3.0]octane (126.7 g; prepared in Reference Example 25) in anhydrous THF (500 ml) was added dropwise for 1.5 hours at 2° C. The mixture was stirred for 10 minutes. To the reaction mixture, diethyl ether (750 ml) and an aqueous saturated solution of sodium sulfate (70 ml) were added. The mixture was stirred for 20 minutes at room temperature and filtered by Celite. The filtrate was concentrated under reduced pressure to obtain the title compound (133.8 g).

TLC: Rf 0.36 (ethyl acetate:acetic acid=50:1); NMR (200 MHz, CDCl$_3$): δ 7.30–7.06 (m, 4H), 5.64–5.24 (m, 2H), 4.77–4.53 (m, 2H), 4.41 (s, 2H), 4.46–3.28 (m, 9H), 3.39 (s, 3H), 3.09–2.68 (m, 2H), 2.50–1.94 (m, 4H), 1.91–1.17 (m, 12H).

REFERENCE EXAMPLE 27

(9α,11α,15α,13E)-6-Acetylthio-9-trimethylsilyloxy-11,15-bis(2-tetrahydropyranyloxy)-16-(3-methoxymethylphenyl)-1,2,3,4,5,17,18,19,20-nonanorprost-13-en

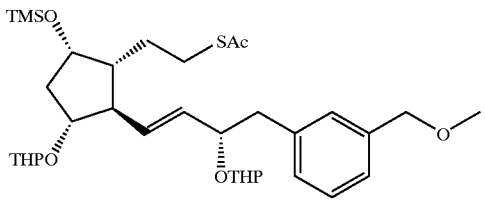

Under an atmosphere of argon gas, a solution of (9α,11α,15α,13E)-6,9-dihydroxy-11,15-bis(2-tetrahydropyranyloxy)-16-(3-methoxymethylphenyl)-1,2,3,4,5,17,18,19,20-nonanorprost-13-en (51.4 g; prepared in Reference Example 26) in anhydrous THF (600 ml) was cooled to –25° C. Thereto, diisopropylethylamine (35.5 ml) was added. At –20° C., mesyl chloride (11.8 ml) was added thereto for 2 minutes. The mixture was stirred for 30 minutes at –10° C.

After entire consumption of the product used for reaction, at –10° C., diisopropylethylamine (35.5 ml) was added thereto. In addition, trimethylsilyl chloride (15.5 ml) was added dropwise thereto for 8 minutes. The mixture was stirred for 1 hour at –10° C.

After termination of reaction, thereto, potassium carbonate (84.6 g) was added at –10° C. and then a solution of potassium thioacetate (34.9 g) in anhydrous DMF (1200 ml) was added dropwise for 1 hour at –10° C. The mixture was stirred for 18 hours at room temperature. Thereto, water (2000 ml) was added. The mixture was extracted with mixture solvent of hexane-ethyl acetate (1:1). The organic layer was washed by water and an aqueous saturated solution of sodium chloride successively, dried over anhydrous magnesium sulfate and concentrated under reduced pressure to obtain the title compound (63.5 g).

TLC: Rf 0.57, 0.53 (hexane:ethyl acetate=2:1).

REFERENCE EXAMPLE 28

(9α,11α,15α,13E)-9-Hydroxy-11,15-bis(2-tetrahydropyranyloxy)-16-(3-methoxymethylphenyl)-17,18,19,20-tetranor-5-thiaprost-13-enoic Acid·Methyl Ester

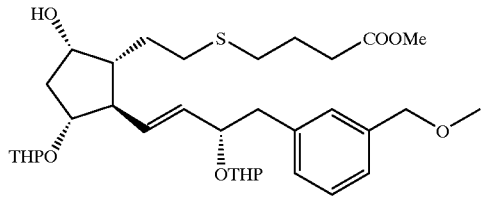

Under an atmosphere of argon gas, to anhydrous THF (200 ml), potassium t-butoxide (27.5 g) was added. Thereto, anhydrous methanol (200 ml) was added dropwise for 6 minutes. The mixture was stirred for 10 minutes. To the reaction solution, a solution of (9α,11α,15α,13E)-6-acetylthio-9-trimethylsilyloxy-11,15-bis(2-tetrahydropyranyloxy)-16-(3-methoxymethylphenyl)-1,2,3,4,5,17,18,19,20-nonanorprost-13-en (63.5 g; prepared in Reference Example 27) and 4-iodobutanoic acid methyl ester (55.8 g; prepared in Reference Example 17) in anhydrous THF (400 ml) was added dropwise for 25 minutes. The mixture was stirred for 30 minutes. The reaction mixture was poured into an aqueous saturated solution of ammonium chloride (1000 ml) and extracted with ethyl acetate. The organic layer was washed by water and an aqueous saturated solution of sodium chloride successively, dried over anhydrous magnesium sulfate and concentrated under reduced pressure. The residue was purified with silica gel column chromatography (hexane-ethyl acetate) to obtain the title compound (51.3 g).

TLC: Rf 0.39 (hexane:ethyl acetate=1:2); NMR (300 MHz, CDCl$_3$): δ 7.31–7.07 (m, 4H), 5.65–5.29 (m, 2H), 4.75–4.59 (m, 2H), 4.43 (s, 2H), 4.31–3.19 (m, 7H), 3.67 (s, 3H), 3.37 (s, 3H), 3.00–2.70 (m, 2H), 2.65–2.03 (m, 10H), 2.01–1.28 (m, 16H).

REFERENCE EXAMPLE 29

(11α,15α,13E)-9-oxo-11,15-bis(2-Tetrahydropyranyloxy)-16-(3-methoxymethylphenyl)-17,18,19,20-tetranor-5-thiaprost-13-enoic Acid·Methyl Ester

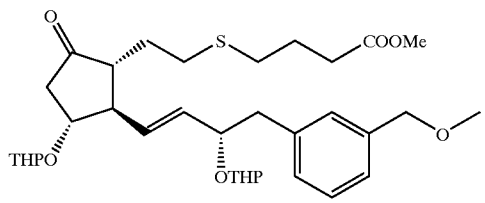

Under an atmosphere of argon gas, to a solution of (9α,11α,15α, 13E)-9-hydroxy-11,15-bis(2-tetrahydropyranyloxy)-16-(3-methoxymethylphenyl)-17,18,19,20-tetranor-5-thiaprost-13-enoic Acid·methyl ester (120.0 g; prepared in Reference Example 28) in anhydrous DMSO (500 ml), triethylamine (161 ml) was added. Thereto, a solution of sulfur trioxide-pyridine complex (92.0 g) in anhydrous DMSO (300 ml) was added for 10 minutes in water bath. The mixture was stirred for 1 hour at room temperature. To the reaction mixture, triethylamine (161 ml) and sulfur trioxide-pyridine complex (92.0 g) were added again. The mixture was stirred.

The reaction mixture was poured into a cooled mixture solution of hexane-ethyl acetate-water (500 ml-500 ml-2000 ml) and extracted with hexane-ethyl acetate (1:1). The organic layer was washed by 1N HCl, water, an aqueous saturated solution of sodium hydrogencarbonate and an aqueous saturated solution of sodium chloride successively, dried over anhydrous magnesium sulfate and concentrated under reduced pressure. The residue was distilled with toluene to obtain the title compound (121.8 g).

TLC: Rf 0.47 (hexane:ethyl acetate=1:1).

EXAMPLE 4

(11α,15α,13E)-9-oxo-11,15-Dihydroxy-16-(3-methoxymethylphenyl)-17,18,19,20-tetranor-5-thiaprost-13-enoic Acid·Methyl Ester

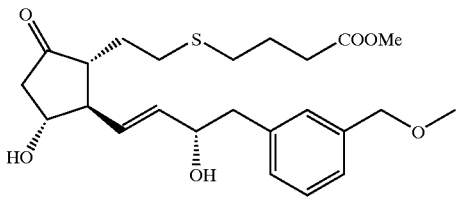

A solution of (9α,11α,15α,13E)-9-hydroxy-11,15-bis(2-tetrahydropyranyloxy)-16-(3-methoxymethylphenyl)-17,18,19,20-tetranor-5-thiaprost-13-enoic acid·methyl ester (121.8 g; prepared in Reference Example 29) in a mixture of acetic acid-THF-water (480 ml-80 ml-240 ml) was stirred for 1.5 hours at 70° C. The reaction mixture was cooled with ice and poured into water (1000 ml).

The mixture was extracted with ethyl acetate. The organic layer was washed by water and an aqueous saturated solution of sodium chloride successively, dried over anhydrous magnesium sulfate and concentrated under reduced pressure. The residue was purified with silica gel column chromatography (ethyl acetate-hexane→ethyl acetate-methanol) to obtain the title compound (32.7 g).

TLC: Rf 0.29 (ethyl acetate:acetic acid=50:1); NMR (500 MHz, CDCl$_3$): δ 7.29 (t, J=7.8 Hz, 1H), 7.20 (s, 1H), 7.17 (d, J=7.8 Hz, 1H), 7.13 (d, J=7.8 Hz, 1H), 5.73 (dd, J=15, 6.5 Hz, 1H), 5.53 (ddd, J=15, 9.0, 1.0 Hz, 1H), 4.46–4.39 (m, 2H), 4.38 (m, 1H), 3.94 (m, 1H), 3.67 (s, 3H), 3.41 (s, 3H), 2.88 (dd, J=14, 5.5 Hz, 1H), 2.82 (dd, J=14, 7.3 Hz, 1H), 2.70 (ddd, J=19, 7.4, 1.1 Hz, 1H), 2.62–2.49 (m, 2H), 2.49 (t, J=7.0 Hz, 2H), 2.42 (t, J=7.3 Hz, 2H), 2.30 (m, 1H), 2.25 (dd, J=19, 10 Hz, 1H), 2.18 (m, 1H), 1.93–1.83 (m, 3H), 1.72–1.63 (m, 1H); Optical rotation:[α]$_D^{26.5}$ −40.3 (c=0.625, CHCl$_3$).

REFERENCE EXAMPLE 30

(1S,5R,6R,7R)-3-oxo-6-(4-(3-Methoxymethylphenyl)-3S-(2-tetrahydropyranyloxy)-1-butyl)-7-(2-tetrahydropyranyloxy)-2-oxabicyclo[3.3.0]octane

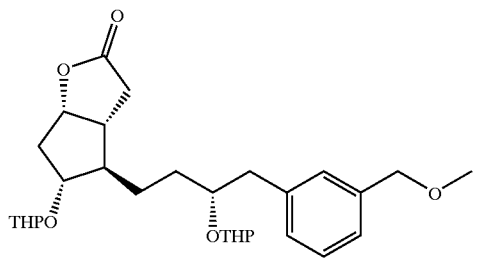

Under an atmosphere of argon gas, to a solution of (1S,5R,6R,7R)-3-oxo-6-(4-(3-methoxymethylphenyl)-3S-(2-tetrahydropyranyloxy)-1-butanyl)-7-(2-tetrahydropyranyloxy)-2-oxabicyclo[3.3.0]octane (100 mg; prepared in Reference Example 25) in methanol (2.0 ml), paradium-carbon (10 mg; 10%) was added. Under an atmosphere of hydrogen gas, the reaction mixture was stirred for 2.5 hours at room temperature. The reaction mixture was filtered by Celite. The filtrate was concentrated. The residue was purified with column chromatography (hexane:ethyl acetate=2/1–1/1) to obtain the title compound (74 mg).

TLC: Rf 0.30 (hexane:ethyl acetate=1:1); NMR (CDCl$_3$, 300 MHz): δ 7.35–7.08 (m, 4H), 4.98–4.94 (m, 1H), 4.70–4.59 and 4.39–4.15 (m, 2H), 4.43 (s, 2H), 4.09–3.75 (m, 3H), 3.60–3.29 (m, 6H), 3.02–2.12 (m, 6H), 2.09–1.40 (m, 18H).

EXAMPLE 5

(11α,15α)-9-oxo-11,15-Dihydroxy-16-(3-methoxymethylphenyl)-17,18,19,20-tetranor-5-thiaprostanoic Acid·Methyl Ester

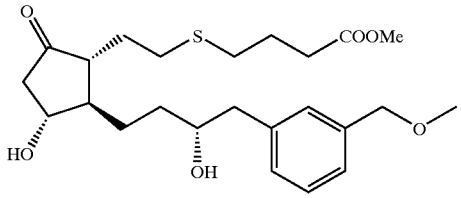

By the same procedures described in Reference Examples 26 to 29 and Example 4 using a compound prepared in Reference Example 30, the title compound was obtained.

TLC: Rf 0.29 (ethyl acetate); NMR (300 MHz, CDCl$_3$): δ 7.36–7.16 (m, 4H), 4.45 (s, 2H), 4.15–4.08 (m, 1H), 3.96–3.90 (m, 1H), 3.67 (s, 3H), 3.42 (s, 3H), 2.90–2.82 (m, 1H), 2.76–2.51 (m, 6H), 2.44 (t, J=7.5 Hz, 2H), 2.31–2.23 (m, 1H), 2.05–1.60 (m, 12H).

EXAMPLE 6

(11α,15α)-9-oxo-11,15-Dihydroxy-16-(3-methoxymethylphenyl)-17,18,19,20-tetranor-5-thiaprostanoic Acid By the same procedures described in Example 3 using a compound prepared in Example 5, the title compound was obtained.

TLC: Rf 0.25 (chloroform:methanol=9:1); NMR (300 MHz, CDCl$_3$): δ 7.35–7.12 (m, 4H), 4.46 (s, 2H), 4.17–4.08 (m, 1H), 4.00–3.90 (m, 1H), 3.44 (s, 3H), 2.91–2.82 (m, 1H), 2.78–2.20 (m, 10H), 2.15–1.60 (m, 12H).

FORMULATION EXAMPLE 1

The following compounds were admixed in conventional method and punched out to obtain 100 tablets each containing 0.5 mg of active ingredient.

(11α,15α,13E)-9-oxo-11,15-dihydroxy-16-(3-methoxymethylphenyl)-17,18,19,20-tetranor-5-thiaprost-13-enoic acid·methyl ester·α-cyclodextrin . . . 250 mg (active ingredient:50 mg)

carboxymethylcellulose calcium . . . 200 mg

Magnesium stearate . . . 100 mg

Micro crystalline cellulose . . . 9.2 g

FORMULATION EXAMPLE 2

The following components were admixed in a conventional method, and the solution was sterilized in a conventional method, placed 1 ml portions into ampoules and freeze-dried in a conventional method to obtain 100 ampoules each containing 0.2 mg of active ingredient.

(11α,15α,13E)-9-oxo-11,15-dihydroxy-16-(3-methoxymethylphenyl)-17,18,19,20-tetranor-5-thiaprost-13-enoic acid·methyl ester·α-cyclodextrin . . . 100 mg (active ingredient:20 mg)

Mannitol . . . 5 g

Distilled water . . . 100 ml

What is claimed is:

1. A 5-thia-ω-substituted phenyl-prostaglandin E derivative of the formula (I)

(wherein, R$^1$ is hydroxy, C1–6 alkyloxy or NR$^6$R$^7$ (in which R$^6$ and R$^7$ is, each independently, hydrogen or C1–4 alkyl), R$^2$ is oxo, halogen or O—COR$^8$ (in which R$^8$ is C1–4 alkyl, phenyl or phenyl(C1–4 alkyl)), R$^3$ is hydrogen or hydroxy, R$^{4a}$ and R$^{4b}$ is, each independently, hydrogen or C1–4 alkyl, R$^5$ is phenyl substituted with the following substituent(s):
  i) 1~3 of
    C1–4 alkyloxy-C1–4 alkyl,
    C2–4 alkenyloxy-C1–4 alkyl,
    C2–4 alkynyloxy-C1–4 alkyl,
    C3–7 cycloalkyloxy-C1–4 alkyl,
    C3–7 cycloalkyl(C1–4 alkyloxy)-C1–4 alkyl,
    phenyloxy-C1–4 alkyl,
    phenyl-C1–4 alkyloxy-C1–4 alkyl,
    C1–4 alkylthio-C1–4 alkyl,
    C2–4 alkenylthio-C1–4 alkyl,
    C2–4 alkynylthio-C1–4 alkyl,
    C3–7 cycloalkylthio-C1–4 alkyl,
    C3–7 cycloalkyl(C1–4 alkylthio)-C1–4 alkyl,
    phenylthio-C1–4 alkyl or
    phenyl-C1–4 alkylthio-C1–4 alkyl,
  ii) C1–4 alkyloxy-C1–4 alkyl and C1–4 alkyl,
    C1–4 alkyloxy-C1–4 alkyl and C1–4 alkyloxy,
    C1–4 alkyloxy-C1–4 alkyl and hydroxy,
    C1–4 alkyloxy-C1–4 alkyl and halogen,
    C1–4 alkylthio-C1–4 alkyl and C1–4 alkyl,
    C1–4 alkylthio-C1–4 alkyl and C1–4 alkyloxy,
    C1–4 alkylthio-C1–4 alkyl and hydroxy or
    C1–4 alkylthio-C1–4 alkyl and halogen,
  iii) haloalkyl or hydroxy-C1–4 alkyl, or
  iv) C1–4 alkyl and hydroxy; and ----- is single bond or double bond, with the proviso that when R$^2$ is O—COR$^8$, C8-C9 represents double bond)

or a non-toxic salt thereof, or a cyclodextrin clathrate thereof.

2. A compound according to claim 1, wherein R$^1$ is hydroxy.

3. A compound according to claim 1, wherein R$^1$ is C1–6 alkoxy.

4. A compound according to claim 1, wherein R$^1$ is NR$^6$R$^7$ (in which all the symbols are as defined in claim 1).

5. A compound according to claim 1, wherein R$^2$ is oxo.

6. A compound according to claim 1, wherein R$^2$ is halogen.

7. A compound according to claim 1, wherein R$^2$ is O—COR$^8$ (in which R$^8$ is as defined in claim 1).

8. A compound according to claim 1, wherein R$^5$ is phenyl substituted with i) 1~3 of
  C1–4 alkyloxy-C1–4 alkyl,
  C2–4 alkenyloxy-C1–4 alkyl,
  C2–4 alkynyloxy-C1–4 alkyl,
  C3–7 cycloalkyloxy-C1–4 alkyl,
  C3–7 cycloalkyl(C1–4 alkyloxy)-C1–4 alkyl,
  phenyloxy-C1–4 alkyl,
  phenyl-C1–4 alkyloxy-C1–4 alkyl,
  C1–4 alkylthio-C1–4 alkyl,
  C2–4 alkenylthio-C1–4 alkyl,
  C2–4 alkynylthio-C1–4 alkyl,
  C3–7 cycloalkylthio-C1–4 alkyl,
  C3–7 cycloalkyl(C1–4 alkylthio)-C1–4 alkyl,
  phenylthio-C1–4 alkyl, or
  phenyl-C1–4 alkylthio-C1–4 alkyl.

9. A compound according to claim 1, wherein R$^5$ is phenyl substituted with ii)
  C1–4 alkyloxy-C1–4 alkyl and C1–4 alkyl, C1–4 alkyloxy-C1–4 alkyl and C1–4 alkyloxy,
C1–4 alkyloxy-C1–4 alkyl and hydroxy,
C1–4 alkyloxy-C1–4 alkyl and halogen,
C1–4 alkylthio-C1–4 alkyl and C1–4 alkyl,
C1–4 alkylthio-C1–4 alkyl and C1–4 alkyloxy,
C1–4 alkylthio-C1–4 alkyl and hydroxy, or
C1–4 alkylthio-C1–4 alkyl and halogen.

10. A compound according to claim 1, wherein $R^5$ is phenyl substituted with iii) haloalkyl or hydroxy-C1–4 alkyl.

11. A compound according to claim 1, wherein $R^5$ is phenyl substituted with iv) C1–4 alkyl and hydroxy.

12. A compound according to claim 1, 2, 5 or 8, which is selected from
 (1) (11α,13E,15α)-9-oxo-11,15-dihydroxy-16-(3-methoxymethylphenyl)-17,18,19,20-tetranor-5-thiaprost-13-enoic acid,
 (2) (11α,13E,15α)-9-oxo-11,15-dihydroxy-16-(3-ethoxymethylphenyl)-17,18,19,20-tetranor-5-thiaprost-13-enoic acid,
 (3) (11α,13E,15α)-9-oxo-11,15-dihydroxy-16-(3-n-propyloxymethylphenyl)-17,18,19,20-tetranor-5-thiaprost-13-enoic acid,
 (4) (11α,15α)-9-oxo-11,15-dihydroxy-16-(3-methoxymethylphenyl)-17,18,19,20-tetranor-5-thiaprostanoic acid,
 (5) (11α,15α,13E)-9-oxo-11,15-dihydroxy-16-methyl-16-(3-methoxymethylphenyl)-17,18,19,20-tetranor-5-thiaprost-13-enoic acid, and
 (6) (15α,13E)-9-oxo-15-hydroxy-16-(3-methoxymethylphenyl)-17,18,19,20-tetranor-5-thiaprost-13-enoic acid.

13. A compound according to claim 1, 3, 5 or 8, which is selected from
 (1) (11α,13E,15α)-9-oxo-11,15-dihydroxy-16-(3-methoxymethylphenyl)-17,18,19,20-tetranor-5-thiaprost-13-enoic acid·methyl ester,
 (2) (11α,13E,15α)-9-oxo-11,15-dihydroxy-16-(3-methoxymethylphenyl)-17,18,19,20-tetranor-5-thiaprost-13-enoic acid·ethyl ester,
 (3) (11α,13E,15α)-9-oxo-11,15-dihydroxy-16-(3-methoxymethylphenyl)-17,18,19,20-tetranor-5-thiaprost-13-enoic acid·n-propyl ester,
 (4) (11α,13E,15α)-9-oxo-11,15-dihydroxy-16-(3-methoxymethylphenyl)-17,18,19,20-tetranor-5-thiaprost-13-enoic acid·i-propyl ester,
 (5) (11α,13E,15α)-9-oxo-11,15-dihydroxy-16-(3-methoxymethylphenyl)-17,18,19,20-tetranor-5-thiaprost-13-enoic acid·n-butyl ester,
 (6) (11α,13E,15α)-9-oxo-11,15-dihydroxy-16-(3-ethoxymethylphenyl)-17,18,19,20-tetranor-5-thiaprost-13-enoic acid·methyl ester,
 (7) (11α,13E,15α)-9-oxo-11,15-dihydroxy-16-(3-n-propyloxymethylphenyl)-17,18,19,20-tetranor-5-thiaprost-13-enoic acid·methyl ester,
 (8) (11α,13E,15α)-9-oxo-11,15-dihydroxy-16-(3-methoxymethylphenyl)-17,18,19,20-tetranor-5-thiaprost-13-enoic acid·t-butyl ester,
 (9) (11α,15α)-9-oxo-11,15-dihydroxy-16-(3-methoxymethylphenyl)-17,18,19,20-tetranor-5-thiaprostanoic acid·methyl ester
 (10) (11α,15α,13E)-9-oxo-11,15-dihydroxy-16-methyl-16-(3-methoxymethylphenyl)-17,18,19,20-tetranor-5-thiaprost-13-enoic acid·methyl ester, and
 (11) (15α,13E)-9-oxo-15-hydroxy-16-(3-methoxymethylphenyl)-17,18,19,20-tetranor-5-thiaprost-13-enoic acid·methyl ester.

14. A compound according to claim 1, 2, 6 or 8, which is selected from (9β,11α,13E,15α)-9-chloro-11,15-dihydroxy-16-(3-methoxymethylphenyl)-17,18,19,20-tetranor-5-thiaprost-13-enoic acid, and (9β,11α,13E,15α)-9-fluoro-11,15-dihydroxy-16-(3-methoxymethylphenyl)-17,18,19,20-tetranor-5-thiaprost-13-enoic acid.

15. A compound according to claim 1, 3, 6 or 8, which is selected from (9β,11α,13E,15α)-9-chloro-11,15-dihydroxy-16-(3-methoxymethylphenyl)-17,18,19,20-tetranor-5-thiaprost-13-enoic acid·methyl ester, and (9β,11α,13E,15α)-9-fluoro-11,15-dihydroxy-16-(3-methoxymethylphenyl)-17,18,19,20-tetranor-5-thiaprost-13-enoic acid·methyl ester.

16. A compound according to claim 1, 2, 5 or 11, which is selected from (11α,13E,15α)-9-oxo-11,15-dihydroxy-16-(3-methyl-4-hydroxyphenyl)-17,18,19,20-tetranor-5-thiaprost-13-enoic acid, and (11α,15α,13E)-9-oxo-11,15-dihydroxy-16-(3-methyl-4-hydroxyphenyl)-17,18,19,20-tetranor-5-thiaprost-13-enoic acid.

17. A compound according to claim 1, 3, 5 or 11, which is selected from (11α,13E,15α)-9-oxo-11,15-dihydroxy-16-(3-methyl-4-hydroxyphenyl)-17,18,19,20-tetranor-5-thiaprost-13-enoic acid·methyl ester, and (11α,15α,13E)-9-oxo-11,15-dihydroxy-16-(3-methyl4-hydroxyphenyl)-17,18,19,20-tetranor-5-thiaprost-13-enoic acid·methyl ester.

18. A process for producing a compound of the formula (Ia) depicted hereafter which is characterized by removal of the protecting group of a compound of the formula (II)

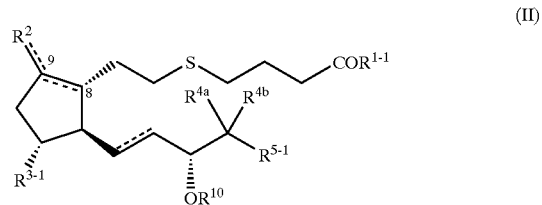

(wherein, $R^{1-1}$ is C1–6 alkyloxy,
 $R^{3-1}$ is hydroxy or hydroxy protected by a protecting group of hydroxy which removed under acidic conditions,
 $R^{10}$ is a protecting group which is removed under acidic conditions,
 $R^{5-1}$ is as as defined for $R^5$ in claim 1, provided that hydroxy in $R^{5-1}$ is protected by a protecting group which is removed under acidic conditions, and the other symbols are as defined in claim 1)
under acidic conditions to obtain a compound of the formula (Ia)

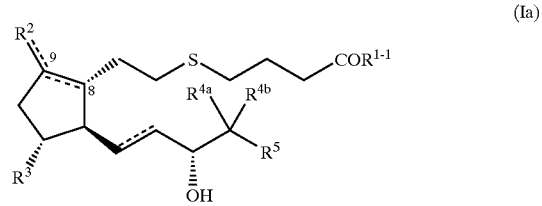

(wherein, $R^3$ and $R^5$ are as defined in claim 1, and the other symbols are as defined hereinbefore).

19. A process for producing a compound of the formula (Ib) depicted hereafter which is characterized by hydrogenolysis of a compound of the formula (Ia)

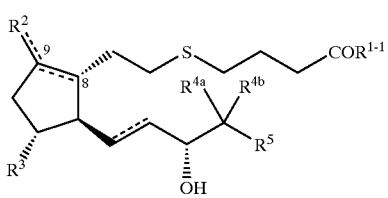

(Ia)

(wherein, all the symbols are as defin claim 1 or 18) using an enzyme or under alkaline conditions to obtain a compound of the formula (Ib)

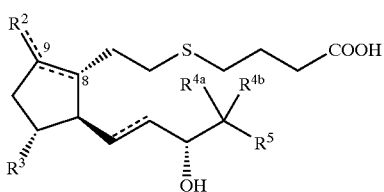

(Ib)

(wherein, all the symbols are as defined hereinbefore).

20. A process for producing a compound of the formula (Ic) depicted hereafter which is characterized by amidation of a compound of the formula (Ib)

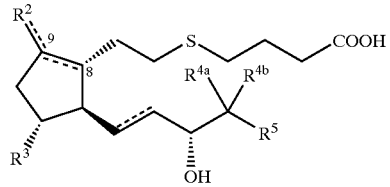

(Ib)

(wherein, all the symbols are as defined in claim 1) with a compound of the formula (III)

$$HNR^6R^7 \quad (III)$$

(wherein, all the symbols are as defined in claim 1) to obtain a compound of the formula (Ic)

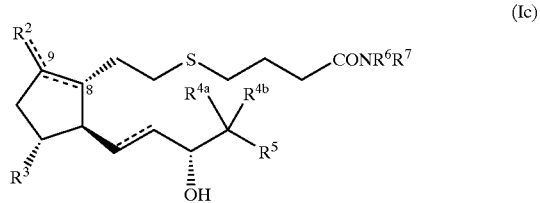

(Ic)

(wherein, all the symbols are as defined hereinbefore).

21. A pharmaceutical composition comprising a 5-thia-ω-substituted phenyl-prostaglandin E derivative depicted in claim 1 or non-toxic salt thereof, orcyclodextrin clathrate thereof as an active ingredient.

* * * * *